US005665873A

United States Patent [19]
Schaffer et al.

[11] Patent Number: 5,665,873
[45] Date of Patent: Sep. 9, 1997

[54] GLUCOCORTICOID RESPONSE ELEMENTS

[75] Inventors: Priscilla A. Schaffer, Holliston; Mary Ann Hardwicke, Brookline, both of Mass.

[73] Assignee: Dana Farber Cancer Institute, Boston, Mass.

[21] Appl. No.: 386,157

[22] Filed: Feb. 9, 1995

[51] Int. Cl.$^6$ .................................................. C07H 21/04
[52] U.S. Cl. ........................................ 536/24.1; 536/23.1
[58] Field of Search ................................. 536/23.1, 24.1

[56] References Cited

U.S. PATENT DOCUMENTS

| | | | |
|---|---|---|---|
| 4,859,609 | 8/1989 | Dull et al. | 436/501 |
| 5,034,506 | 7/1991 | Summerton et al. | 528/391 |
| 5,071,773 | 12/1991 | Evans et al. | 436/501 |
| 5,077,284 | 12/1991 | Loria et al. | 514/171 |
| 5,221,669 | 6/1993 | Anand et al. | 514/58 |
| 5,272,071 | 12/1993 | Chappel | 435/172.3 |
| 5,298,429 | 3/1994 | Evans et al. | 436/501 |
| 5,312,732 | 5/1994 | Evans et al. | 435/69.1 |
| 5,512,483 | 4/1996 | Mader et al. | 435/320.1 |

FOREIGN PATENT DOCUMENTS

| | | |
|---|---|---|
| 0 219 214 A1 | 4/1987 | European Pat. Off. . |
| 0 316 717 A1 | 5/1989 | European Pat. Off. . |
| WO 88/00975 | 2/1988 | WIPO . |

OTHER PUBLICATIONS

Frink et al. Proceedings of the National Academy of Sciences USA, 78(10):6139–6143.
Lomonte. Journal of General Virology, 76:1835–1841.
Alroy, et al., "DNA binding analysis of glucocorticoid receptor specificity", *Nucl. Acids. Res.* 20:1045–1052 (1992)
*Antiviral Agents Bulletin* 5: 161–163, 1992.
Beato, M., "Gene regulation by steroid hormones", *Cell* 1989, 56, 335–344.
Berg, "DNA Binding Specificity of Steroid Receptors" *Cell* 57: 1065–1068 (1989).
Beyer, C.F., et al., "Penetrating keratoplasty in rabbits induces latent HSV-1 reactivation when corticosteroid are used" *Curr. Eye. Res.* 8(12): 1323–1329 (Dec. 1989).
BioWorld Today., "The antisense drug Isis Pharmaceutical Inc. is developing for treating cytomegalovirus . . . " *Daily Biotechnology Newspaper* 1993, December 20, 3 of 4.
Brown, G.A. and Field, H.J., "Experimental reactivation of bovine herpesvirus 1 (BHV–1) by means of corticosteroid in an . . . " *Arch. Virol.* 112(1–2) 81–101 (1990).
Challberg et al., "Animal Virus DNA Replication" *Ann. Rev. Biochem.* 58:671–717 (1989).
Chandler, V.L. et al., "DNA sequences bound specifically by glucocorticoid receptor in vitro render a heterologous promoter hormone . . . " *Cell* 33(2): 489–499 (Jun. 1983).
Chang et al., "Identification of Herpesvirus–Like DNA Sequences in AIDS–Associated Kaposi's Sarcoma" *Science* 266: 1865–1869 (1995).
Cohen, Jack and Hogan, Michael E., "The New Genetic Medicines" *Scientific American* 76–82 Dec. 1994.

Curvers, V. et al., "Effect of dexamethasone on the mean plaque size of bovine herpesvirus 1" *Ann Rech Vet* 16 (1): 80–85 (1985).
Davies et al., "Role of Cell–Mediated Immunity in the Recovery of Cattle from Primary and Recurrent Infections with Infectious . . . ", *Infect. Immun.* 8:510–518 (1973).
DeLuca et al., "Activation of Immediate–Early, Early, and Late Promoters by Temperature–Sensitive and Wild–Type Forms of Herpes . . . " *Mol. Cell Biol.* 5:1997–2008 (1985).
Dieken, E.S. and Miesfeld, R.L., "Transcriptional transactivation functions localized to the glucocorticoid receptor N . . . " *Mol. Cell. Biol.* 12(2): 589–597 (Feb. 92).
Dietrich, J.B. et al., "Antagonism of glucocorticoid induction of Epstein–Barr virus early antigens by different . . . " *J. Steroid Biochem.* 24(1): 417–421 (Jan. 1986).
Edington, N. et al., "Cytomegalovirus excretion in gnotobiotic pigs" *J. Hyg.* (Lond) 77(2): 283–290, (Oct. 1976).
Edington, N. et al., "Experimental reactivation of equid herpesvirus 1 (EHV 1) following the administration of corticosteroid" *Equine. Vet. J.* 17(5): 369–372 (Sep. 85).
Edwards, S. and Roeder, P.L., "Attempted reactivation of latent bovine herpesvirus 1 infection in calves by . . . " *Vet. Microbiol.* 8(6): 563–569 (Nov. 1983).
Epsy, M.J. et al., "Effect of treatment of shell vial cell cultures with dimethyl sulfoxide and dexamethasone for . . . " *J. Clin. Microbiol.* 26(6) 1091–1093 (Jun. 1988).
Evans, R.N., "The Steroid and Thyroid Hormone Receptor Superfamily", *Science* 240:889–895 (1988).
Fechheimer, et al., "Transfection of Mammalian Cells with Plasmid DNA by Scrape Loading and Sonication Loading", *Proc. Natl. Acad. Sci., USA*, 84:8463–8467 (1987).
Fedorko, D.P. et al., "Effect of treatment of shell vial cell cultures with dimethyl sulfoxide and dexamethasone . . . " *Diagn. Microbiol. Infect. Dis.* 13(1): 41–44 (Feb. 1990).
Forbes, B.A. et al., "The effects of a promoter of cell differentiation and selected hormones on human cytomegalovirus . . . " *J. Infect. Dis.* 162(1): 39–45 (Jul. 1990).
Frankel et al., "Cellular Uptake of the Tat Protein from Human Immunodeficiency Virus" *Cell* 55: 1189–1193 (1988).
Ghosh, "A relational database of transcription factors" *NAR* 18: 1749–1756 (1990).
Green et al., "Autonomous Functional Domains of Chemically Synthesized Human Immunodeficiency Virus Tat Trans–Activator Protein" *Cell* 55: 1179–1188 (1988).

(List continued on next page.)

*Primary Examiner*—Douglas W. Robinson
*Assistant Examiner*—Thanda Wai
*Attorney, Agent, or Firm*—Panitch Schwarze Jacobs & Nadel, P.C.

[57] ABSTRACT

The invention features an isolated herpesvirus glucocorticoid response element comprising a DNA sequence comprising two consensus hexanucleotide glucocorticoid receptor binding sequences having at least five nucleotides positioned therebetween. The invention further features compositions and methods for preventing herpesvirus replication and reactivation.

20 Claims, 10 Drawing Sheets

OTHER PUBLICATIONS

Hanton, G. et al, "Development of specific antibodies mediating antibody-dependent cell-mediated cytotoxicity following . . . " *Vet. Microbiol.* 11(1-2) 51–59 (1986).

Hard et al., "Cooperativity and Specificity in the Interactions between DNA and the Glucocorticoid Receptor DNA-Binding Domain", *Biochem.* 29:5358–5364 (1990).

Hayward et al., "Anatomy of herpes simplex virus DNA: Evidence for four populations of molecules that differ in the . . . " *PNAS USA* 72: 4243–4247 (1975).

Hollenberg et al., "Primary structure and expression of a functional human glucocorticoid receptor cDNA" *Nature* 318: 635–641 (1985).

Honess et al., "Regulation of Herpesvirus Macromolecular Synthesis" *J. Virol.* 14: 8–19 (1974).

Iida, S. et al., "Properties of glucocorticoid receptors in Epstein–Barr Virus–transformed lymphocytes from patients . . . " *Cancer Res.* 49(8 Suppl) 2214s–2216s (Apr. 15, 1989).

Jones et al., "A Cellular DNA-Binding Protein that Activates Eukaryotic Transcription and DNA Replication" *Cell* 48: 79–89 (1987).

Koment, R.W., "Restriction to human cytomegalovirus replication in vitro removed by physiological levels of cortisol" *J. Med. Virol.* 27(1): 44–47 (Jan. 1989).

Buetti et al., "Distinct Sequence Elements Involved in the Glucocorticoid Regulation of the Mouse Mammary Tumor Virus . . . " *J. Mol. Biol.* 190:379–389 (1986)

Kupfer, Stuart R. and Summers, William C., "Identification of a Glucocorticoid–Responsive Element in Epstein–Barr Virus" *J. of Virology* 64: 1984–1990 (1990).

Lafer et al., "Antibodies Specific for Left-Handed Z-DNA" *PNAS USA* 78:3546–3550 (1981).

Lafer et al., "Z-DNA-binding Proteins in *Escherichia coli* Purification, Generation of Monoclonal Antibodies and Gene Isolation", *J. Mol. Biol.* 203(2): 511–516 (1988).

Lancz, G.J. et al., "Glucocorticoid–mediated establishment of an antiviral state coincident with other glucocorticoid–. . . " *J. Gen. Virol.* 66 (Pt.10) 2249–2252 (Oct. 1985).

Lathey, J.L. and Spector, S.A., "Unrestricted replication of human cytomegalovirus in hydrocortisone–treated macrophages" *J. Virol.* 65(11): 6371–6375 (Nov. 1991).

Leib, et al., "A Deletion Mutant of the Latency–Associated Transcript of Herpes Simplex Virus Type 1 Reactivates from the Latent State with . . . " *J. Virol.* 63:2893–2900 (1989).

Leib, David A., et al., "Immediate–Early Regulatory Gene Mutants Define Different Stages in the Establishment and Reactivation . . . " *J. of Virology* 63:759–768 (1989).

Leonardi, G.P. and Lipson, S.M. "Enhanced detection of cytomegalovirus in shell vial culture . . . " *Int. J. Med. Virol. Parasitol. Infec. Dis.* 277(1): 90–99 (Jun. 1992).

Lipsett, M.B. et al., "Cortisol Resistance in man" *Adv. Exp. Med. Biol.* 196: 97–109 (1986).

Li, S.B. and Fong, C.K., "Detection of human cytomegalovirus early and late antigen and DNA production in cell culture . . . " *J. Med. Virol.* 30(2): 97–102 (Feb. 1990).

MacGregor, M.P. et al, "Effects of cyclosporine and cortisone on the pathogenesis of primary infection with cytomegalovirus . . . " *J. Infect. Dis.* 153(3) 503–510 (Mar. 86).

Magrath, I.T. et al., "Enhancement of Epstein–Barr virus replication in producer cell lines by a combination of low . . . " *Virology* 97(2): 477–481 (Sep. 1979).

McGeoch et al., "The Complete DNA Sequence of the Long Unique Region in the Genome of HerpesSimplex Virus Type 1" *J. Gen. Virol.* 69: 1531–1574 (1988).

Meek et al., "Inhibition of HIV–1 Protease in Infected T-Lymphocytes by Synthetic Peptide Analogues" *Nature* 343: 90–92 (1990).

Melnick et al., "Studies on Herpes Simplex Virus and Cancer" *Cancer Res.* 36:845–856 (1976).

Minagawa, Hiroko et al., "Detection of Herpes Simplex Virus Type 1–Encoded RNA by Polymerase Chain Reaction: Different Pattern . . . " *J. of General Virology* 75: 647–650 (1994).

Nielson et al., "Sequence–Selective Recognition of DNA by Strand Displacement with a Thymine–Substituted Polyamide" *Science* 254: 1497–1500 (1991).

Ohtaki, S. et al., "Activation of cytomegalovirus infection in immunosuppressed cynomolgus monkeys inoculated . . . " *Acta. Pathol. Jpn.* 36(10): 1537–1552 (Oct. 1986).

Paek, I. and Axel, R. "Glucocorticoids enhance stability of human growth hormone mRNA" *Mol. Cell. Biol.* 7(4):1496–1507 (Apr. 1987).

Papkoff, J. and Ringold, G.M., "Use of the mouse mammary tumor virus long terminal repeat to promote steroid–inducible . . . " *J. Virol.* 52(2) 420–430 (Nov. 1984).

Pearce, "A mechanistic basis for distinct mineralocorticoid and glucocorticoid receptor transcriptional specificities" *Steroids* 59:153–159 (1994).

Pertuiset et al., "Physical Mapping and Nucleotide Sequence of a Herpes Simplex Virus Type 1 Gene Required for Capsid Assembly", *J. Virol.* 63:2169–2179 (1989).

Pina, B. et al., "Hormonal Induction of transfected genes depends on DNA topology" *Mol. Cell. Biol.* 10(2): 625–633 (Feb. 1990).

Polvino–Bodnar, et al., "Herpes Simplex Virus Type 1 ori$_L$ Is Not Required for Virus Replication or for the establishment . . . " *J. Virol.* 61: 3528–3535 (1987).

Rabinovitch, T. et al., "In vivo reactivation of latent murine cytomegalovirus in the eye by immunosuppressive . . . " *Invest. Ophthalmol. Vis. Sci.* 31(4) 657–663 (Apr. 1990).

Rixon et al., "Identification of the genes encoding two capsid proteins of herpes simplex virus type 1 by amino acid sequencing", *J. Gen. Virol.* 71:1211–1214 (1990).

Rock, D. et al., "Characterization of Dexamethasone–Induced Reactivation of Latent Bovine Herpesvirus 1" *J. of Virology* 66:2484–2490 (1992).

Rootman, David S. et al., "corneal Nerves are Necessary for Adrenergic Reactivation of Ocular Herpes" *Inves. Ophthal. & Visual Sci.* 29/3: 351–355 (1988).

Sandri–Goldin et al., "Expression of Herpes Simplex Virus β and μ Genes Integrated in Mammalian Cells and Their Induction by a α Gene Product", *Mol.Cell.Biol.* 3:2028–2044 (1983).

Schoenbaum, M.A. et al., "Pseudorabies virus latency and reactivation in vaccinated swine" *Am. J. Vet. Res.* 51 (3): 334–338 (Mar. 1990).

Schuster, C. et al., "Activation of Epstein–Barr virus promoters by a growth–factor and a glucocorticoid" *Febs. Lett.* 284(1): 82–86 (Jun. 17, 1991).

Shimeld, C. et al., "An improved model of recurrent herpetic eye disease in mice" *Curr Eye Res.* 8 (11): 1193–1205 (Nov. 1989).

Shimeld, C., et al., "Reactivation of Latent Infection and Induction of Recurrent Herpetic Eye Disease in Mice" *J. of Gen. Virology* 71:397–404 (1990).

Sinclair, A.J. et al., "Reciprocal antagonism of steroid hormones and BZLF1 in switch between Epstein–Bart virus latent . . . " *J. Virol.* 66(1): 70–77 (Jan. 1992).

Spaete et al., "the herpes simplex virus amplicon: Analyses of cis–acting replication functions" *Proc. Natl. Acad. Sci. USA* 82: 694–698 (1985).

Spivak et al., "Detection of Herpes Simplex Virus Type 1 Transcripts during Latent Infection in Mice" *J. Virol.* 61: 3841–3847 (1987).

Stevens, et al., "RNA Complementary to a Herpesvirus α Gene mRNA is Prominent in Latently Infected Neurons" *Science* 235: 1056–1059 (1987).

Stow, et al., "Characterization of the $TR_s/IR_s$ Origin of DNA Replication of Herpes Simplex Virus Type 1" *Virology* 130:427–438 (1983).

Stroop, William G. and Schaefer, Douglas C., "Production of Encephalitis Restricted to the Temporal Lobes by . . . " *J. of Infec. Dis.* 153: 721–731 (1986).

Sundar, S.K. et al., "Retinoic acid and steroids inhibit Epstein–Barr virus–induced nuclear antigen, DNA . . . " *Anticancer Res.* 4(6): 415–418 (Nov.–Dec. 1984).

Tanaka, J. et al., "Dexamethasone enhances human cytomegalovirus replication in human epithelial cell cultures" *Virology* 136(2): 448–452 (Jul. 30, 1984).

Tanaka, J. et al., "Enhanced replication of human cytomegalovirus in human fibroblasts treated with dexamethasone" *J. Gen. Virol.* 65 (Pt. 10) 1759–1767 (Oct. 1984).

Thiele, G.M. and Woods, G.L., "The effect of dexamethasone on the detection of cytomegalovirus in tissue culture and by . . . " *J. Virol. Methods* 22(2–3): 319–328 (Dec. 1988).

Tomita, M. et al., "Glucocorticoid Receptors in Epstein–Barr virus–transformed human lymphocytes" *Horm. Metab. Res.* 17(12): 674–678 (Dec. 1985).

Tsai et al., "Molecular Interactions of Steroid Hormone Receptor with Its Enhancer Element: Evidence for Receptor Dimer Formation", *Cell* 55: 361–369 (1988).

Uchida, Y. et al., "Varicella dendritic keratitis" *Am. J. Ophthalmol.* 89(2): 259–262 (Feb. 1980).

Vamvakopoulos, N.C. et al., "Lack of dexamethasone modulation of mRNAs involved in the glucocorticoid signal transduction . . . " *Steroids* 57(6): 282–287 (Jun. 1992).

Wagner, Richard W., "Gene Inhibition Using Antisense Oligodeoxynucleotides" *Nature* 373: 333–335 (1994).

Weller et al., "Genetic Analysis of Temperature–Sensitive Mutants Which Define the Gene for the Major Herpes Simplex Virus Type 1 DNA–Binding . . . " *J. Virol.* 45:354–366 (1983).

Weller, Sandra K. et al., "Cloning, Sequencing, and Functional Analysis of $ori_L$, a Herpes Simplex Virus Type 1 DNA–Synthesis" *Mol. and Cell. Biology* 5:930–942 (1985).

West, P.G. et al., "Enhanced detection of cytomegalovirus in confluent MRC–5 cells treated with dexamethasone and . . . " *J. Clin. Microbiol.* 26(12): 2510–2514 (Dec. 1988).

West, P.G. and Baker, W.W., "Enhancement by calcium of the detection of cytomegalovirus in cells treated with . . . " *J. Clin. Microbiol.* 28(8): 1708–1710 (Aug. 1990).

Whetstone, C. et al., "Two different strains of an alphaherpesvirus can establish latency in the same tissue . . . " *Arch. Virol.* 107(1–2) 27–34 (1989).

Wong et al., "Elements in the Transcriptional Regulatory Region flaking Herpes Simplex Virus Type 1 oriS Stimulate Origin Function" *J. Virol.* 65:2601–2611 (1991).

Yei et al., "Identification and Characterization of the Herpes Simplex Virus Type 2 Gene Encoding the Essential Capsid Protein ICP32/VP19c", *J.Virol.* 64:1124–1134 (1990).

Zwaagstra et al., "Activity of Herpes Simplex Virus Type 1 Latency–Associated Transcript (LAT) Promoter in . . . " *J. Virol.* 64:5019–5028 (1990).

Scheidereit, Claus et al., "The glucocorticoid receptor binds to defined nucleotide sequences near the promoter of mouse mammary tumour virus", *Nature* 304:749–752 (1983).

Rousseau et al., "Glucocorticoid Agonist and Antagonist Activity of 17,21–Acetonide Steroids", (1983) *J. Steroid Biochem.* 18–3:237–244.

Green et al., "In Vivo Reactivation of Herpes Simplex Virus in Rabbit Trigeminal Ganglia: Electrode Model", (1981) *Infect. Immun.* 34–1:69–74.

Frink et al., "Uninfected Cell Polymerase Efficiently Transcribes Early but not Late Herpes Simplex Virus Type 1 mRNA", (1981) *Proc. Natl. Aced. Sci. USA* 78–10:6139–6143.

Lockshon et al., "Cloning and Characterization of $ori_{L2}$, a Large Palindromic DNA Replication Origin of Herpes Simplex Virus Type 2", (1986) *J. Virol:* 58–2:513–521.

Knopf et al., "The DNA Replication Origins of Herpes Simplex Virus Type 1 Strain Angelotti", (1986) *Nucleic Acids Research* 14–21:8655–8667.

Devlin et al., "Random Peptide Libraries: A Source of Specific Protein Binding Molecules", (1990) *Science* 249:404–406.

Bielinska et al., "Regulation of Gene Expression with Double–Stranded Phosphorothioate Oligonucleotides", (1990) *Science* 250:997–1000.

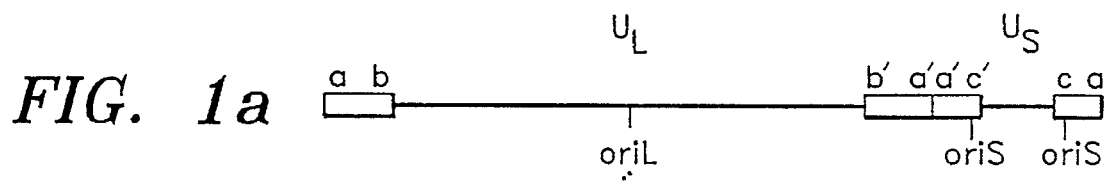
FIG. 1a
FIG. 1b
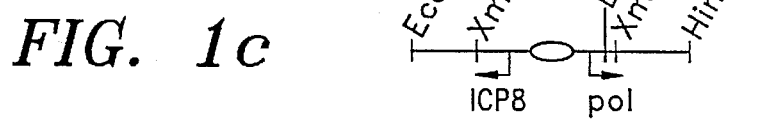
FIG. 1c
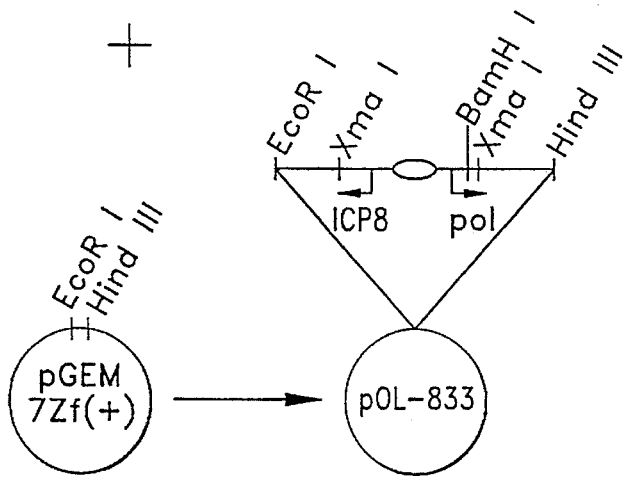

A.

B.

C.

GLUCORTICOID RESPONSE ELEMENT (GRE)

CONSENSUS  5'- A G $\genfrac{}{}{0pt}{}{A}{G}$ A C A (n)$_3$ T G T $\genfrac{}{}{0pt}{}{T}{C}$ C T -3'

OriL  5'- T G T C C T (n)$_{18}$ A G G A C A -3'

OriS  5'- C G T C C C (n)$_{18}$ A G G G C G -3'

ICP6  5'- A G G A C A (n)$_6$ T G T C C T -3'

```
                              A   A   T
                              A   A   T
                             ·G   A   T
                              A   A   T
                              A   A   T
                              A   A   T
                              A   A   T
····GGGGCCGCCGGGT   T   A
                              A   T
                              T   A
                              T   A
                              A   T
                              T   A
                              C   G
                              G   C
                              C   G
                              C   G
                              G   C
                              G   C
                              T   A
                              G   C
                              C   G
                              G   C
                              G   C
                              G   C
                              T   A
                              G   C
                              G   C
                              C   G
                              C   G
                              C   G         oriL
                              G   C
····CGCGTCATCA   TACGTCACGCT····
```

*FIG. 7b*

SEQUENCE LISTING ( 1 ) GENERAL INFORMATION:

( i i i ) NUMBER OF SEQUENCES: 88

( 2 ) INFORMATION FOR SEQ ID NO:1:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

AGRACANNNT GTYCT 15

( 2 ) INFORMATION FOR SEQ ID NO:2:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

TGTCCTNNNN NNNNNNNNNN NNNNAGGACA 30

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
AGGACANNNN  NNTGTCCT                                                      18
```

( 2 ) INFORMATION FOR SEQ ID NO:4:

( i ) SEQUENCE CHARACTERISTICS:
        ( A ) LENGTH: 92 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
AAAAAAAGTG  AACGCGAAGC  GTTCGCACTT  TGTCCTAATA  ATATATATAT  TATTAGGACA    60
AAGTGCGAAC  GCTTCGCGTT  CTCACTTTTT  TT                                    92
```

( 2 ) INFORMATION FOR SEQ ID NO:5:

( i ) SEQUENCE CHARACTERISTICS:
        ( A ) LENGTH: 91 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
AAAAGAAGTG  AACGCGAAGC  GTTCGCACTT  CGTCCCAATA  TATATATATT  ATTAGGGCGA    60
AGTGCGAGCA  CTGGCGCCGT  GCCCGACTCC  G                                     91
```

( 2 ) INFORMATION FOR SEQ ID NO:6:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
AGRACANNNT  GTYCT                                                         15
```

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

```
CGTCCCNNNN  NNNNNNNNNN  NNNNAGGGCG                                        30
```

( 2 ) INFORMATION FOR SEQ ID NO:8:

( i ) SEQUENCE CHARACTERISTICS:
    ( A ) LENGTH: 91 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:8:

```
GGGGCCGCCG GGTAAAAGAA GTGAGAACGC GAAGCGTTCG CACTTCGTCC CAATATATAT      60
ATATTATTAG GGCGAAGTGC GAGCACTGGC G                                     91
```

( 2 ) INFORMATION FOR SEQ ID NO:9:

( i ) SEQUENCE CHARACTERISTICS:
        ( A ) LENGTH: 163 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
CGCGTCATCA GCCGGTGGGC GTGGCCGCTA TTATAAAAAA AGTGAGAACG CGAAGCGTTC       60
GCACTTTGTC CTAATAATAT ATATATTATT AGGACAAAGT GCGAACGCTT CGCGTTCTCA      120
CTTTTTTTAT AATAGCGGCC ACGCCCACCG GCTACGTCAC GCT                        163
```

( 2 ) INFORMATION FOR SEQ ID NO:10:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
GTTCGCACTT TGTCCTAATA ATATATATAT TAGGACAAAG TGCGAACG                   48
```

( 2 ) INFORMATION FOR SEQ ID NO:11:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
GTTCGCACTT CGTCCCAATA ATATATATAT TGGGACGAAG TGCGAACG                   48
```

( 2 ) INFORMATION FOR SEQ ID NO:12:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
TGTTCTNNNN NNNNNNAGGA CA                                               22
```

( 2 ) INFORMATION FOR SEQ ID NO:13:

( i ) SEQUENCE CHARACTERISTICS:
           ( A ) LENGTH: 28 base pairs
           ( B ) TYPE: nucleic acid
           ( C ) STRANDEDNESS: single
           ( D ) TOPOLOGY: linear ( i i ) MOLECULE TYPE: DNA (genomic)

( x i ) SEQUENCE DESCRIPTION: SEQ ID NO:13:

AGGACANNNN NNNNNNNNNN NNTGTTCT                                                    28

( 2 ) INFORMATION FOR SEQ ID NO:14:

( i ) SEQUENCE CHARACTERISTICS:
           ( A ) LENGTH: 31 base pairs
           ( B ) TYPE: nucleic acid
           ( C ) STRANDEDNESS: single
           ( D ) TOPOLOGY: linear ( i i ) MOLECULE TYPE: DNA (genomic)

( x i ) SEQUENCE DESCRIPTION: SEQ ID NO:14:

TGTCCTNNNN NNNNNNNNNN NNNNNAGGAC A                                          31

( 2 ) INFORMATION FOR SEQ ID NO:15:

( i ) SEQUENCE CHARACTERISTICS:
           ( A ) LENGTH: 27 base pairs
           ( B ) TYPE: nucleic acid
           ( C ) STRANDEDNESS: single
           ( D ) TOPOLOGY: linear ( i i ) MOLECULE TYPE: DNA (genomic)

( x i ) SEQUENCE DESCRIPTION: SEQ ID NO:15:

TGTTCTNNNN NNNNNNNNNN NAGGACA                                                       27

( 2 ) INFORMATION FOR SEQ ID NO:16:

( i ) SEQUENCE CHARACTERISTICS:
           ( A ) LENGTH: 17 base pairs
           ( B ) TYPE: nucleic acid
           ( C ) STRANDEDNESS: single
           ( D ) TOPOLOGY: linear ( i i ) MOLECULE TYPE: DNA (genomic)

( x i ) SEQUENCE DESCRIPTION: SEQ ID NO:16:

TGTTCTNNNN NAGAACA                                                                      17

( 2 ) INFORMATION FOR SEQ ID NO:17:

( i ) SEQUENCE CHARACTERISTICS:
           ( A ) LENGTH: 19 base pairs
           ( B ) TYPE: nucleic acid
           ( C ) STRANDEDNESS: single
           ( D ) TOPOLOGY: linear ( i i ) MOLECULE TYPE: DNA (genomic)

( x i ) SEQUENCE DESCRIPTION: SEQ ID NO:17:

TGTCCTNNNN NNNAGGACA                                                                   19

( 2 ) INFORMATION FOR SEQ ID NO:18:

( i ) SEQUENCE CHARACTERISTICS:
           ( A ) LENGTH: 30 base pairs
           ( B ) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:18:

AGAACANNNN NNNNNNNNNN NNNNTGTTCT 30

(2) INFORMATION FOR SEQ ID NO:19:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:19:

AGAACANNNN NNNNNNNNTG TCCT 24

(2) INFORMATION FOR SEQ ID NO:20:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:20:

AGGACANNNN NNNNNNTGTT CT 22

(2) INFORMATION FOR SEQ ID NO:21:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:21:

TGTTCTNNNN NNNNNNTGTT CT 22

(2) INFORMATION FOR SEQ ID NO:22:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:22:

AGGACANNNN NNNNNNNNNT GTTCT 25

(2) INFORMATION FOR SEQ ID NO:23:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

( x i ) SEQUENCE DESCRIPTION: SEQ ID NO:23:

AGAACANNNN NNNNNNNNNN NNNNTGTTCT                30

( 2 ) INFORMATION FOR SEQ ID NO:24:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

TGTCCTNNNN NNAGAACA                18

( 2 ) INFORMATION FOR SEQ ID NO:25:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

AGGACANNNN NNNNNNNAG GACA                24

( 2 ) INFORMATION FOR SEQ ID NO:26:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

TGTCCTNNNN NNNNNNNNNA GGACA                25

( 2 ) INFORMATION FOR SEQ ID NO:27:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

TGTCCTNNNN NNNNNNNNNN NNAGGACA                28

( 2 ) INFORMATION FOR SEQ ID NO:28:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

TGTCCTNNNN NNNNNNNNNN NNNNNNAGAA CA                32

( 2 ) INFORMATION FOR SEQ ID NO:29:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

TGTTCTNNNN NNNNNNNNNA GAACA         25

( 2 ) INFORMATION FOR SEQ ID NO:30:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

TCTCCTNNNN NNNNNNNNNA GAACA         25

( 2 ) INFORMATION FOR SEQ ID NO:31:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

TGTYCTNNNA GRACA         15

( 2 ) INFORMATION FOR SEQ ID NO:32:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

TGTYCTNNNN AGRACA         16

( 2 ) INFORMATION FOR SEQ ID NO:33:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

TGTYCTNNNN NAGRACA         17

( 2 ) INFORMATION FOR SEQ ID NO:34:

( i ) SEQUENCE CHARACTERISTICS:
        ( A ) LENGTH: 18 base pairs
        ( B ) TYPE: nucleic acid ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

TGTYCTNNNN NNAGRACA 18

( 2 ) INFORMATION FOR SEQ ID NO:35:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

TGTYCTNNNN NNNAGRACA 19

( 2 ) INFORMATION FOR SEQ ID NO:36:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:36:

TGTYCTNNNN NNNNAGRACA 20

( 2 ) INFORMATION FOR SEQ ID NO:37:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:37:

TGTYCTNNNN NNNNNAGRAC A 21

( 2 ) INFORMATION FOR SEQ ID NO:38:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:38:

TGTYCTNNNN NNNNNNAGRA CA 22

( 2 ) INFORMATION FOR SEQ ID NO:39:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:39:

TGTYCTNNNN NNNNNNNAGR ACA                23

( 2 ) INFORMATION FOR SEQ ID NO:40:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:40:

TGTYCTNNNN NNNNNNNNAG RACA               24

( 2 ) INFORMATION FOR SEQ ID NO:41:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:41:

TGTYCTNNNN NNNNNNNNNA GRACA              25

( 2 ) INFORMATION FOR SEQ ID NO:42:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:42:

TGTYCTNNNN NNNNNNNNNN AGRACA             26

( 2 ) INFORMATION FOR SEQ ID NO:43:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:43:

TGTYCTNNNN NNNNNNNNNN NAGRACA            27

( 2 ) INFORMATION FOR SEQ ID NO:44:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:44:

TGTYCTNNNN NNNNNNNNNN NNAGRACA           28

( 2 ) INFORMATION FOR SEQ ID NO:45:

( i ) SEQUENCE CHARACTERISTICS:
  ( A ) LENGTH: 29 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:45:

TGTYCTNNNN NNNNNNNNNN NNNAGRACA    29

( 2 ) INFORMATION FOR SEQ ID NO:46:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:46:

TGTYCTNNNN NNNNNNNNNN NNNNAGRACA    30

( 2 ) INFORMATION FOR SEQ ID NO:47:

( i ) SEQUENCE CHARACTERISTICS:
  ( A ) LENGTH: 31 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:47:

TGTYCTNNNN NNNNNNNNNN NNNNNAGRAC A    31

( 2 ) INFORMATION FOR SEQ ID NO:48:

( i ) SEQUENCE CHARACTERISTICS:
  ( A ) LENGTH: 32 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:48:

TGTYCTNNNN NNNNNNNNNN NNNNNNAGRA CA    32

( 2 ) INFORMATION FOR SEQ ID NO:49:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:49:

AGRACANNNT GTYCT    15

( 2 ) INFORMATION FOR SEQ ID NO:50:

( i ) SEQUENCE CHARACTERISTICS:
  ( A ) LENGTH: 16 base pairs
  ( B ) TYPE: nucleic acid

```
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:50:

AGRACANNNN  TGTYCT                                                      16

( 2 ) INFORMATION FOR SEQ ID NO:51:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:51:

AGRACANNNN  NTGTYCT                                                     17

( 2 ) INFORMATION FOR SEQ ID NO:52:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:52:

AGRACANNNN  NNTGTYCT                                                    18

( 2 ) INFORMATION FOR SEQ ID NO:53:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:53:

AGRACANNNN  NNNTGTYCT                                                   19

( 2 ) INFORMATION FOR SEQ ID NO:54:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:54:

AGRACANNNN  NNNNTGTYCT                                                  20

( 2 ) INFORMATION FOR SEQ ID NO:55:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: DNA (genomic)
```

( x i ) SEQUENCE DESCRIPTION: SEQ ID NO:55:

AGRACANNNN NNNNNTGTYC T　　　　　　　　　　　　　　　　　　　　　　　　21

( 2 ) INFORMATION FOR SEQ ID NO:56:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:56:

AGRACANNNN NNNNNNTGTY CT　　　　　　　　　　　　　　　　　　　　　　　　22

( 2 ) INFORMATION FOR SEQ ID NO:57:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:57:

AGRACANNNN NNNNNNNTGT YCT　　　　　　　　　　　　　　　　　　　　　　　　23

( 2 ) INFORMATION FOR SEQ ID NO:58:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:58:

AGRACANNNN NNNNNNNNTG TYCT　　　　　　　　　　　　　　　　　　　　　　　　24

( 2 ) INFORMATION FOR SEQ ID NO:59:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:59:

AGRACANNNN NNNNNNNNNT GTYCT　　　　　　　　　　　　　　　　　　　　　　　　25

( 2 ) INFORMATION FOR SEQ ID NO:60:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:60:

AGRACANNNN NNNNNNNNNN TGTYCT　　　　　　　　　　　　　　　　　　　　　　　26

( 2 ) INFORMATION FOR SEQ ID NO:61:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:61:

AGRACANNNN NNNNNNNNNN NTGTYCT                    27

( 2 ) INFORMATION FOR SEQ ID NO:62:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:62:

AGRACANNNN NNNNNNNNNN NNTGTYCT                  28

( 2 ) INFORMATION FOR SEQ ID NO:63:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:63:

AGRACANNNN NNNNNNNNNN NNNTGTYCT                29

( 2 ) INFORMATION FOR SEQ ID NO:64:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:64:

AGRACANNNN NNNNNNNNNN NNNNTGTYCT               30

( 2 ) INFORMATION FOR SEQ ID NO:65:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:65:

AGRACANNNN NNNNNNNNNN NNNNTGTYC T              31

( 2 ) INFORMATION FOR SEQ ID NO:66:

( i ) SEQUENCE CHARACTERISTICS:
        ( A ) LENGTH: 32 base pairs
        ( B ) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:66:

AGRACANNNN NNNNNNNNN NNNNNNTGTY CT  32

(2) INFORMATION FOR SEQ ID NO:67:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:67:

GGTACANNNT GTTCT  15

(2) INFORMATION FOR SEQ ID NO:68:

(i) SEQUENCE CHARACTERISTICS:
  (A) LENGTH: 16 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:68:

GGTACANNNN TGTTCT  16

(2) INFORMATION FOR SEQ ID NO:69:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:69:

GGTACANNNN NTGTTCT  17

(2) INFORMATION FOR SEQ ID NO:70:

(i) SEQUENCE CHARACTERISTICS:
  (A) LENGTH: 18 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:70:

GGTACANNNN NNTGTTCT  18

(2) INFORMATION FOR SEQ ID NO:71:

(i) SEQUENCE CHARACTERISTICS:
  (A) LENGTH: 19 base pairs
  (B) TYPE: nucleic acid
  (C) STRANDEDNESS: single
  (D) TOPOLOGY: linear (ii) MOLECULE TYPE: DNA (genomic)

( x i ) SEQUENCE DESCRIPTION: SEQ ID NO:71:

GGTACANNNN NNNTGTTCT                    19

( 2 ) INFORMATION FOR SEQ ID NO:72:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:72:

GGTACANNNN NNNNTGTTCT                   20

( 2 ) INFORMATION FOR SEQ ID NO:73:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:73:

GGTACANNNN NNNNNTGTTC T                 21

( 2 ) INFORMATION FOR SEQ ID NO:74:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:74:

GGTACANNNN NNNNNNTGTT CT                22

( 2 ) INFORMATION FOR SEQ ID NO:75:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:75:

GGTACANNNN NNNNNNNTGT TCT               23

( 2 ) INFORMATION FOR SEQ ID NO:76:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:76:

GGTACANNNN NNNNNNNNTG TTCT              24

( 2 ) INFORMATION FOR SEQ ID NO:77:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:77:

GGTACANNNN NNNNNNNNNT GTTCT     25

( 2 ) INFORMATION FOR SEQ ID NO:78:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:78:

GGTACANNNN NNNNNNNNNN TGTTCT     26

( 2 ) INFORMATION FOR SEQ ID NO:79:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:79:

GGTACANNNN NNNNNNNNNN NTGTTCT     27

( 2 ) INFORMATION FOR SEQ ID NO:80:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:80:

GGTACANNNN NNNNNNNNNN NNTGTTCT     28

( 2 ) INFORMATION FOR SEQ ID NO:81:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:81:

GGTACANNNN NNNNNNNNN NNNTGTTCT     29

( 2 ) INFORMATION FOR SEQ ID NO:82:

( i ) SEQUENCE CHARACTERISTICS:
    ( A ) LENGTH: 30 base pairs
    ( B ) TYPE: nucleic acid 5,665,873

57
-continued ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:82:

GGTACANNNN NNNNNNNNNN NNNNTGTTCT                                    30

( 2 ) INFORMATION FOR SEQ ID NO:83:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:83:

GGTACANNNN NNNNNNNNNN NNNNNTGTTC T                                  31

( 2 ) INFORMATION FOR SEQ ID NO:84:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:84:

GGTACANNNN NNNNNNNNNN NNNNNNTGTT CT                                 32

( 2 ) INFORMATION FOR SEQ ID NO:85:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:85:

AGAACANNNT GTTCT                                                    15

( 2 ) INFORMATION FOR SEQ ID NO:86:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:86:

CGGAATTCCG TGGTTGCCGT CTTGGGCTTT                                    30

( 2 ) INFORMATION FOR SEQ ID NO:87:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

(x i) SEQUENCE DESCRIPTION: SEQ ID NO:87:

CCCAAGCTTG GGGCCGCCGA CTTTCCTCCG G  31

(2) INFORMATION FOR SEQ ID NO:88:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (i i) MOLECULE TYPE: DNA (genomic)

(x i) SEQUENCE DESCRIPTION: SEQ ID NO:88:

CGTCCCNNNN NNNNNNNNNN NNNNGGGACG  30

GLUCOCORTICOID RESPONSE ELEMENTS

GOVERNMENT SUPPORT

Portions of this invention were made using U.S. Government support (NIH Grant No. RO1 AI 28537). The U.S. Government may have certain rights in the invention.

FIELD OF THE INVENTION

The field of the invention is immunosuppression and potentiation of virus replication and reactivation during immunosuppression, and in particular, immunosuppression affected by glucocorticoids, and herpesvirus replication and reactivation.

BACKGROUND OF THE INVENTION

Herpesviruses are a family of large double stranded DNA-containing viruses many members of which are important human pathogens. A ubiquitous property of the herpesviruses is their capacity to cause both acute (productive) and latent infections in the human host, each of which is characterized by marked differences in patterns of vital transcription, DNA replication and in DNA structure.

Members of the herpesvirus family which are human pathogens include herpes simplex virus type 1, herpes simplex virus type 2, varicella zoster virus, Epstein Barr virus, cytomegalovirus, human herpes virus type 6, human herpes virus type 7, and that human herpesvirus which is associated with Kaposi's sarcoma (Chang et al., 1995, Science 266:1865–1869). Of these, herpes simplex virus type 1 (HSV-1) has been most intensively studied. This virus is the causative agent of a variety of diseases in humans including, but not limited to, gingivostomatitis, genital herpes, meningoencephalitis, keratoconjunctivitis, eczema herpeticum and systemic herpes virus disease of the newborn.

The herpes simplex virus type 1 (HSV-1) genome is a linear double-stranded DNA molecule composed of two unique components, designated unique long (UL) and unique short (US), each of which is flanked by inverted repeat sequences (Hayward, et al., 1975, Proc. Natl. Acad. Sci. USA. 72:4243–4247; McGeoch et al., 1988, J. Gen. Virol. 69:1531–1574). The HSV-1 genome contains three origins of DNA replication, one located within $U_L$ (oriL) and two within the repeat sequences flanking $U_s$ (oriS) (Challberg et al., 1989, Ann. Rev. Biochem. 58:671; Spaete et al., 1985, Proc. Natl. Acad. Sci. USA 82:694; Stow et al., Virology 130:427).

Expression of HSV-1 genes during productive infection proceeds in a coordinate and sequential manner (Honess et al., 1974, J. Virol. 14:8–19). The classification of HSV-1 proteins into broad sequential groups, immediate-early (IE), early (E), delayed early (DE), and late (L), is based on the kinetics of synthesis of individual viral transcripts and proteins, the effects of various metabolic inhibitors on DNA, RNA and protein synthesis, and studies using viral mutants.

In contrast to the complex sequence of events which occurs during productive infection, vital gene expression during latency is relatively simple. In latently infected cells, viral gene expression is limited to the latency-associated transcripts (LATs), a family of transcripts ranging in size from 2.0 to >8 kilobase pairs (kb) (Stevens et al., 1987, Science 235:1056–1059; Spivak et al., J. Virol. 61:3841–3847; Zwaagstra et al., 1990, J. Virol. 64:5019–5028). The factors which mediate the switch from productive infection to latency and vice versa are not known.

It has been reported that treatment of HSV-1 latently infected mice with a combination of U.V. irradiation, cyclophosphamide and dexamethasone results in an increased level of reactivation of virus in the mouse eye compared with treatment with cyclophosphamide and dexamethasone alone. Once reactivation has begun, treatment with cyclophosphamide and dexamethasone may increase the duration of virus shedding from the eye (Shimeid et al., 1990, J. Gen. Virol. 71:397–404; Rootman et al., 1988, Investigative Opthalomology and Visual Science 29/3:351–356).

Glucocorticoid response elements (GREs) are DNA sequences that serve as binding sites for a hormone-inducible transcription-activating complex. According to the current model, steroid hormones bind to their specific receptors located within the cytoplasm (for glucocorticoids) and the nucleus (for progestins and estradiol). Formation of glucocorticoid/receptor complexes in the cytoplasm is followed by translocation of these complexes to the nucleus. Hormone/receptor complexes within the nucleus bind to a GRE and activate transcription of cellular genes. A GRE in its simplest form has been defined by the palindromic sequence 5"-AG$^A$/$_G$ACAnnnTGT$^T$/$_C$CT-3'[SEQ ID NO:1] (Kupfer et al., 1990, J. Virol., 64: 1984–1990; Berg, 1989, Cell 57: 1065–1068). A GRE was first identified as a element which responded to glucocorticoids, but is now recognized as the common response element for glucocorticoids, progestins, mineralocorticoids and androgens (Schreidereit et al., 1983, Nature 304:749–752; Beato, 1989, Cell 56:335–344). The distinct physiological effects of the different hormones result from differences in the levels of hormone receptor expression within a cell, enzymatic effects on different receptors prior to binding of complexes to DNA, and differential interaction with other sites on the DNA (Pearce, Steroids, 1994; 59: 153–159).

Immunosuppression of humans is frequently associated with reactivation of herpesvirus infection (including HSV) and recurrence of clinical disease. Until the instant invention, this reactivation was believed result from the inability of the immunosuppressed host to clear virus during spontaneous reactivation. The instant invention establishes a direct role for immunosuppressive compounds in virus replication and reactivation, and thereby provides an understanding of the mechanism by which virus is reactivated in the immunosuppressed host. Thus, the instant invention satisfies a long felt need for methods and compositions designed to facilitate immunosuppression of a host, which immunosuppression does not result in reactivation and replication of virus.

SUMMARY OF THE INVENTION

The invention features an isolated herpesvirus glucocorticoid response element comprising a DNA sequence comprising two consensus hexanucleotide glucocorticoid receptor binding sequences having at least five nucleotides positioned therebetween.

In one aspect of the invention, the herpesvirus glucocorticoid response element is from a herpesvirus selected from the group consisting of herpes simplex virus type 1, herpes simplex virus type 2, human cytomegalovirus, human herpesvirus type 6, bovine herpesvirus, herpes virus samairi, murine cytomegalovirus and Ictalurid herpesvirus.

In another aspect of the invention, the herpesvirus glucocorticoid response element is from a herpesvirus selected from the group consisting of herpes simplex virus type 1, herpes simplex virus type 2, human cytomegalovirus and human herpesvirus type 6.

In yet another aspect, the herpesvirus glucocorticoid response element of the invention is from herpes simplex virus type 1. Preferably, the herpesvirus glucocorticoid response element of the invention is herpes simplex virus type 1 oriL glucocorticoid response element or herpes simplex virus type 1 ICP6 glucocorticoid response element. More preferably, the herpesvirus glucocorticoid response element has the sequence 5'-TGTCCT $(N)_{18}$ AGGACA -3'[SEQ ID NO:3]or 5'-AGGACA $(N)_6$ TGTCCT -3'[SEQ ID NO:3].

In an embodiment of the invention, the hexanucleotide glucocorticoid receptor binding sequences of the herpesvirus glucocorticoid response element of the invention have from five to twenty nucleotides positioned therebetween. Preferably, the hexanucleotide glucocorticoid receptor binding sequences have from six to eighteen nucleotides positioned therebetween.

The invention also features an isolated nucleic acid sequence of 18 to 100 nucleotides complementary to a DNA sequence comprising a herpesvirus glucocorticoid response element. The herpesvirus glucocorticoid response element comprises two consensus hexanucleotide glucocorticoid receptor binding sequences having at least five nucleotides positioned therebetween.

In one aspect, the isolated nucleic acid from a herpesvirus selected from the group consisting of herpes simplex virus type 1, herpes simplex virus type 2, human cytomegalovirus, human herpesvirus type 6, bovine herpesvirus, herpes virus samairi, murine cytomegalovirus and Ictalurid herpesvirus.

In another aspect, the isolated nucleic acid from a herpesvirus selected from the group consisting of herpes simplex virus type 1, herpes simplex virus type 2, human cytomegalovirus and human herpesvirus type 6.

In yet another aspect, the isolated nucleic acid is from herpes simplex virus type 1. Preferably, the herpesvirus glucocorticoid response element is herpes simplex virus type 1 oriL glucocorticoid response element or herpes simplex virus type 1 ICP6 glucocorticoid response element. More preferably, the sequence of the herpesvirus glucocorticoid response element is 5'-TGTCCT $(N)_{18}$ AGGACA -3'[SEQ ID NO:]or 5'- AGGACA $(N)_6$ TGTCCT -3'[SEQ ID NO:].

Also featured in the invention is an antibody capable of binding to a DNA sequence comprising a herpesvirus glucocorticoid response element, the herpesvirus glucocorticoid response element comprising two consensus hexanucleotide glucocorticoid receptor binding sequences having at least five nucleotides positioned therebetween.

In one aspect, the herpesvirus glucocorticoid response element is from a herpesvirus selected from the group consisting of herpes simplex virus type 1, herpes simplex virus type 2, human cytomegalovirus, human herpesvirus type 6, bovine herpesvirus, herpes virus samairi, murine cytomegalovirus and Ictalurid herpesvirus.

In another aspect, the herpesvirus is selected from the group consisting of herpes simplex virus type 1, herpes simplex virus type 2, human cytomegalovirus and human herpesvirus type 6. In yet another aspect, the herpesvirus is herpes simplex virus type 1, and the herpesvirus glucocorticoid response element is preferably, herpes simplex virus type 1 oriL glucocorticoid response element or herpes simplex virus type 1 ICP6 glucocorticoid response element. More preferably, the herpesvirus glucocorticoid response element has the sequence 5'- TGTCCT $(N)_{18}$ AGGACA -3'[SEQ ID NO:3]or 5'- AGGACA $(N)_6$ TGTCCT -3'[SEQ ID NO:3].

Further featured in the invention is a method of inhibiting replication of a herpesvirus. The method comprises adding to a cell containing a herpesvirus genome a compound capable of inhibiting the function of a herpesvirus glucocorticoid response element, which element comprises two consensus hexanucleotide glucocorticoid receptor binding sequences having at least five nucleotides positioned therebetween.

In one embodiment of the method, the herpesvirus glucocorticoid response element is from a herpesvirus selected from the group consisting of herpes simplex virus type 1, herpes simplex virus type 2, human cytomegalovirus, human herpesvirus type 6, bovine herpesvirus, herpes virus samairi, murine cytomegalovirus and Ictalurid herpesvirus.

In another embodiment, the compound is an isolated nucleic acid sequence of 18 to 100 nucleotides complementary to a DNA sequence comprising a herpesvirus glucocorticoid response element.

In yet another embodiment, the compound is an antibody capable of binding to a DNA sequence comprising a herpesvirus glucocorticoid response element.

In yet another embodiment, the compound is an a glucocorticoid analog capable of interfering with binding of a glucocorticoid to a DNA sequence comprising a herpesvirus glucocorticoid response element.

Also featured in the invention is a method of inhibiting reactivation of a herpesvirus. The method comprises adding to a cell containing a herpesvirus genome a compound capable of inhibiting the function of a herpesvirus glucocorticoid response element.

The invention also provides a method of inhibiting reactivation of a herpesvirus in a animal. This method comprises administering to an animal infected with a herpesvirus a compound capable of inhibiting the function of a herpesvirus glucocorticoid response element.

In these latter two methods, the herpesvirus is selected from the group consisting of herpes simplex virus type 1, herpes simplex virus type 2, human cytomegalovirus, human herpesvirus type 6, bovine herpesvirus, herpes virus samairi, murine cytomegalovirus and Ictalurid herpesvirus. Further, the compound is preferably an isolated nucleic acid sequence, or an antibody.

Also included in the invention is a compound capable of inhibiting the function of a herpesvirus glucocorticoid response element.

The invention further features a method of screening a candidate antiherpesviral compound. The method comprises adding the compound to cells containing a plasmid encoding a herpesvirus glucorticoid response element. The effect of the compound on the function of the glucorticoid response element is measured and reduced function of the glucorticoid response element in the presence of the compound compared with the absence of the compound is an indication that the compound is an antiherpesviral compound. Preferably, the function of the glucorticoid response element is measured in a transcription assay or a DNA replication assay.

The invention further features a method of screening a candidate antiherpesviral compound wherein the method comprises administering the compound to an animal infected with a herpesvirus, the compound being predicted to interfere with the function of a herpesvirus glucorticoid response element. The level of replication of the virus in the animal is measured, and a reduced level of replication of the virus in the presence of the compound compared with the level of virus replication in the absence of the compound is an indication that the compound is an antiherpesviral compound. In another aspect of this method, the compound is administered to the animal in conjunction with an immunosuppressive glucocorticoid.

There is provided yet another method of screening a candidate antiherpesviral compound comprising administering a compound to an animal infected with a herpesvirus. The compound is predicted to interfere with the function of a herpesvirus glucocorticoid response element. The level of reactivation of the virus in the animal is measured and a reduced level of reactivation of the virus in the presence of the compound compared with the level of virus reactivation in the absence of the compound is an indication that the compound is an antiherpesviral compound. In another aspect of this method, an immunosuppressive agent is administered to the animal in conjunction with the compound.

DESCRIPTION OF THE DRAWINGS

FIG. 1 comprising parts (A), (B) and (C) is a diagram depicting the cloning strategy for the 833 bp oriL-containing plasmid pOL-833. (A) diagram of the HSV genome indicating the locations of the internal and terminal repeat sequences (a, b, c and b', a', c'), the unique long (UL) and the unique short (US) components of the genome and the three origins of replication (oriL and oriS). (B) Diagram of the 833 bp oriL containing fragment generated by PCR using two oligonucleotide primers. These primers add new restriction sites at the 5'(EcoRI) and 3'(HindIII) ends of the oriL-containing fragment. The oval represents the 144 bp palindrome. (C) Diagram of the 833 bp PCR-generated oriL-containing fragment. The 833 bp oriL fragment was digested with EcoRI and HindIII and ligated into pGEM7Zf(+) to generate pOL-833. The arrows represent the transcriptional start sites of the divergently transcribed genes encoding ICP8 and DNA polymerase (pol) that flank oriL.

FIG. 6 depicts the DNA sequence of the consensus [SEQ ID NO:6] GRE, the HSV-1 oriL GRE [SEQ ID NO:2], the HSV-1 oriS degenerate GRE [SEQ ID NO:7], and the GRE found in the promoter of HSV-1 ICP6 [SEQ ID NO:3].

FIG. 7 depicts a comparison of the DNA sequence of HSV-1 oriL and oriS [SEQ ID NOS: 8 and 9, respectively]. The dots indicate the nucleotides which differ between oriL and oriS. The hexanucleotides of the GRE are indicated by boxes.

DETAILED DESCRIPTION

Figure 2A:
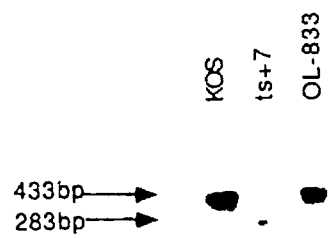
FIG. 2 comprising parts (A) and (B) depicts Southern blot analysis of vital DNA in oriL-containing plasmid pOL-833. Vital (KOS and ts+7) and plasmid (pOL-833) DNAs were digested with XmaI and BamHI, electrophoresed in a 1.2% agarose gel, and transferred to a nitrocellulose filter. The DNA on the filter was hybridized to a nick-translated 433 bp XmaI to BamHI oriL-containing fragment diagrammed in (B).

A new class of GREs has been discovered, termed Group II GREs, which are different from all other known GREs.

termed Group I GREs. Discovery of Group II GREs and analysis of their function provides evidence for a direct role for immunosuppressive compounds in virus replication and reactivation, particularly herpes simplex virus replication and reactivation. It is now possible, based upon the discovery of Group II GREs, to provide methods and compositions which facilitate immunosuppression of a host, which immunosuppression does not result in reactivation and replication of virus.

The Group II GREs of the invention were discovered first in the HSV-1 genome. Other Group II GREs have also been discovered in other viral genomes using the information obtained for HSV-1.

The Group II GRE in HSV-1 is different from other heretofore known GREs (Group I) in that it comprises two consensus hexanucleotide glucocorticoid binding sites which are separated by at least five nucleotides. Group I GREs, primarily though not exclusively found in host cell genomes, comprise two hexanucleotides GR binding sites separated by only three nucleotides (Evans, 1988, Science 240:889–895). The features of the Group II GRE, i.e., two hexanucleotide binding sites separated by at least five nucleotides, serve to distinguish these GREs from Group I GREs.

In the HSV-1 genome, unique GREs have been found in both oriL and in the ICP6 promoter sequence. The elements present in oriL and in ICP6 comprise two hexanucleotide sequences separated by eighteen or six nucleotides, respectively. A partial GRE has been discovered in a herpesvirus by Kupfer et al. (1990, J. Virol. 64:1984–1990). This GRE has only one consensus hexanucleotide binding site. Thus, the GREs of Group II, discovered in HSV-1 (and in other herpesviruses and other non-herpesviruses described herein) are distinct from other known GREs (Group I).

Additional herpesvirus GREs also encompassed by the invention, include those found in other human herpesviruses, such as herpes simplex virus type 2 (HSV-2), human cytomegalovirus (HCMV), and human herpesvirus type 6 (HHV-6); and in other animal herpesviruses, such as bovine herpesvirus type 4 (BHV-4), Ictalurid herpesvirus (IHV), murine cytomegalovirus (MCMV), and herpesvirus samairi (HVS) (Table 1). Further, Group II GREs also included in the instant invention which are similar to those now discovered in HSV-1 have been discovered in human immunodeficiency virus (HIV) and in human papillomavirus (HPV) (Table 1).

TABLE 1

| Group I Consensus Sequence | | GRE Sequence |
|---|---|---|
| Group I Consensus Sequence | | $AG^{A}/_{G}ACA\ (N)_3\ TGT^{T}/_{C}CT$ [SEQIDNO:1] |
| Group II GRE'S | | |
| Herpesvirus | Classification | GRE Sequence |
| HSV-1 | alpha | AGGACA $(N)_6$ TGTCCT [SEQIDNO:3] |
| | | TGTCCT $(N)_{18}$ AGGACA [SEQIDNO:2] |
| HSV-2 | alpha | TGTCCT $(N)_{18}$ AGGACA [SEQIDNO:2] |
| BHV-4 | alpha | TGTTCT $(N)_{10}$ AGGACA [SEQIDNO:12] |
| IHV-1 | alpha | TGTCCT $(N)_{18}$ AGGACA [SEQIDNO:2] |
| VZV | alpha | none |
| PRV | alpha | none |

TABLE 1-continued

| Herpesvirus | Classification | GRE Sequence |
|---|---|---|
| HCMV | beta | AGGACA $(N)_{16}$ TGTTCT [SEQIDNO:13] |
| | | TGTCCT $(N)_{19}$ AGGACA [SEQIDNO:14] |
| | | TGTTCT $(N)_{15}$ AGGACA [SEQIDNO:15] |
| MCMV | beta | TGTTCT $(N)_5$ AGAACA [SEQIDNO:16] |
| | | TGTCCT $(N)_7$ AGGACA [SEQIDNO:17] |
| HHV6 | beta | AGAACA $(N)_{18}$ TGTTCT [SEQIDNO:18] |
| | | AGAACA $(N)_{12}$ TGTCCT [SEQIDNO:19] |
| HVS | gamma | AGGACA $(N)_{10}$ TGTTCT [SEQIDNO:20] |
| | | TGTTCT $(N)_{10}$ TGTTCT [SEQIDNO:21] |
| Nonherpesvirus | | GRE Sequence |
| HIV-1 | | AGGACA $(N)_{13}$ TGTTCT [SEQIDNO:22] |
| HTLV-1 | | AGAACA $(N)_{18}$ TGTTCT [SEQIDNO:23] |
| | | TGTCCT $(N)_6$ AGAACA [SEQIDNO:24] |
| HPV-10 | | AGGACA $(N)_{12}$ TGTCCT [SEQIDNO:25] |
| | | TGTCCT $(N)_{13}$ AGGACA [SEQIDNO:26] |
| HPV-15 | | TGTCCT $(N)_{16}$ AGGACA [SEQIDNO:27] |
| HPV-19 | | TGTCCT $(N)_{20}$ AGAACA [SEQIDNO:28] |
| HPV-27 | | TGTTCT $(N)_{13}$ AGAACA [SEQIDNO:29] |
| HPV-34 | | TGTCCT $(N)_{13}$ AGAACA [SEQIDNO:30] |

To discover the Group II GREs listed in Table I, based upon the information obtained on the HSV-1 oriL GRE (the discovery of which is described below), a computer search was conducted wherein the HSV-1 genome was examined for the presence of each hexanucleotide component of the GRE individually, to determine if any two inverted hexanucleotides were in close proximity to each other. A search of the entire genome using the original database, i.e. the transcriptional regulatory element search of Ghosh (1990. NAR 18:1749–1756) described herein, proved impractical since a search for transcriptional elements in 800 bp of oriL sequence revealed numerous elements, most of which were irrelevant. A search of the HSV-1 genome targeting the hexanucleotide sequence revealed the presence of an additional GRE in the HSV-1 genome located in the promoter regulatory region of the UL39 (ICP6) gene. This gene encodes a protein comprising the large subunit of ribonucleotide reductase (at the C-terminal end) and having kinase activity which is located at the N-terminal end of the protein. This GRE matches the Group I consensus GRE sequence (FIG. 6) except that the hexanucleotides located within the ICP6 promoter are separated by six rather than three nucleotides. This GRE is therefore designated as a Group II GRE.

To determine whether other herpesvirus and other non-herpesviruses also contain GREs, a search of herpesvirus and non-herpesvirus DNA sequences available in the GenBank database was conducted. For this search, the Genetics Computer Group Sequence Analysis software, Version 7.3 1-UNEX (Genetics Computer Group, 1991), and the program, FINDPATTERN was used. Until the present invention, GREs having hexanucleotide sequences separated by greater then three nucleotides were not known. In addition, a single GRE hexanucleotide, as opposed to two hexanucleotides separated by three nucleotides, is believed to be only minimally functional in cells (Kuhnel et al., 1986, J. Mol. Biol. 190:379–389). In accordance with the discovery of the GREs of the instant invention, a search for other Group II GREs was conducted wherein the following sequences were used to search available herpesvirus and other non-herpesvirus DNA sequences in the GenBank database. The following three different DNA sequences were used in the search:

5'- TGT$^T/_C$CT (N)$_{3–20}$AG$^A/_G$ACA -3'[SEQ ID NOS:31–48], HSV-1 oriL GRE, 5'- AG$^A/_G$ACA (N)$_{3–20}$TGT$^T/_C$CT -3'[SEQ ID NOS: 49–66], HSV-1 ICP6 GRE, 5'- GGTACA (N)$_{3–20}$TGTTCT -3'[SEQ ID NOS:67–84], (Evans, 1988, Science 240:889–895—refers to hexanucleotides separated by only three nucleotides). Heretofore unknown herpesvirus GRE elements, included in the present invention, were revealed by this search. The results of this computer search are shown in Table 1. Thus, it has been discovered that herpes simplex virus type 2 contains one GRE which is identical to that present in the HSV-1 oriL sequence. Human cytomegalovirus contains three GREs two of which are identical to that in HSV-1 oriL except that the spacing between the two hexanucleotide components in human cytomegalovirus differs from that in HSV-1 oriL. The third human cytomegalovirus sequence differs from the HSV-1 ICP6 GRE by one base pair in the hexanucleotide sequence and additionally, the spacing between the two hexanucleotide components of each of these GREs also differs. Two GREs are present in human herpesvirus type 6, each of which is similar but not identical to that found in HSV-1 ICP6 in the hexanucleotide components, and each of which differs in the spacing between the two hexanucleotides. Additional herpesvirus Group II GREs are present in several animal herpesviruses including bovine herpesvirus type 4, Ictalurid herpesvirus, murine cytomegalovirus, and herpesvirus samairi (Table 1).

A GRE has also been discovered in the genome of Epstein Barr virus (EBV) which comprises two hexanucleotide sequences separated by three nucleotides. Thus, this GRE resembles the GRE sequences of Group I. The sequence of the

5'- AGAACA (N)$_3$ TGTTCT -3'[SEQ ID NO:85].

In a manner similar to that described for herpesviruses, other sequenced viral genomes were searched for the presence of the unique Group II GRE of the invention. As shown in Table 1, Group II GREs were discovered in HIV, HTLV-1 and in various serotypes of HPV. As noted above, each of these viruses undergoes a latent or a low grade persistent infection in humans. Thus, similar to the case for herpesviruses, the GREs in HIV, HTLV-1 and in HPV may play a role in potentiation of replication and reactivation of virus from these states.

In the experiments described below, a GRE-like element present in HSV-1 oriS was shown to be non-functional (FIG. 6 and Table 4). The hexanucleotide of oriS differs from that in oriL by four nucleotides. These changes are indicated by underlining in the sequences given below.

oriL: TGTCCT (N)$_{18}$ AGGACA[SEQ ID NO:2]
oriS: CGTCCC (N)$_{18}$ AGGGCG[SEQ ID NO:7]

The nucleotide differences between oriL and oriS render the oriS GRE-like sequences non-functional.

Tests described herein show that the Group II GREs of the invention, for example, that present in the oriL region of HSV-1, is responsive to glucocorticoid stimulation in a cell-based DNA replication assay. Further, purified glucocorticoid receptor (GR) binds to that region of oriL which contains the GRE. Thus, HSV-1 GRE functions to bind glucocorticoid receptor (GR) and thus, should therefore stimulate replication of HSV-1 upon treatment of cells with glucocorticoids. In view of the present invention, it appears that immunosuppression of patients using glucocorticoids may result in direct stimulation of replication and reactivation of HSV from latency. Support for this conclusion is derived from the fact that (1) most HSV infections in immunocompromised patients are not primary infections, but are caused by reactivation; (2) clinical findings in immunocompromised patients are typically significantly more serious than in non-immunocompromised patients; (3) the present invention has established a direct interaction between a glucocorticoid and a unique GRE in the HSV-1 genome, which interaction results in glucocorticoid-induced viral DNA replication.

With respect to the unique Group II GREs of the invention which are now discovered in HIV, HTLV-1 and HPV, a shared feature among these viruses and the herpesviruses is their ability to establish latent and low grade persistent infections in the host. In each instance (i.e., during the course of a herpesvirus, HIV, HTLV-1 or HPV infection), virus may be stimulated to replicate, thereby exacerbating the respective disease for which that virus is the etiological agent. The data described herein provide evidence that glucocorticoids may play a role in reactivation of herpesviruses using a mechanism involving GREs. Glucocorticoids are also likely to play a role in stimulation of replication and reactivation of HIV and HPV using a similar mechanism.

The present invention features compositions and methods capable of discriminating between the unique Group II GREs of the invention and that of Group I GREs, which compositions and methods are therefore useful for selectively interfering with GRE function thereby preventing virus replication following reactivation. The compositions and methods of the invention thus serve as a basis for therapies which may be administered to patients undergoing immunosuppressive treatment, which therapies are specifically designed so as to not interfere with immunosuppression while acting to prevent virus replication and reactivation.

The compositions and methods of the invention therefore also serve as a basis for therapy for treating established HSV infection which reactivate in the host in response to naturally produced glucocorticoids during for example, situations involving stress, absorption of U.V. light, etc.

The Group II GRE of the invention comprises two GRE hexanucleotides having at least five nucleotides positioned therebetween. Group I GREs comprise two GRE hexanucleotide sequences having only three nucleotides positioned therebetween. To effect immunosuppression of a patient, commonly a glucocorticoid is administered to the patient. Glucocorticoid effects activation of GR which then binds to GRE. Binding of GR to GRE results in eventual immunosuppression of the patient. Compounds which specifically interfere with the activity of Group II GREs, but which do not interfere with the activity of Group I GREs, are predicted to prevent stimulation of replication and reactivation of virus in a patient without affecting the immunosuppressive capability of the compound. The invention includes an isolated Group II GRE, preferably a herpesvirus GRE, comprising a viral DNA sequence comprising two hexanucleotide DNA sequences having at least five nucleotides positioned therebetween. The isolated herpesvirus GRE of the invention is substantially homologous to any one of the heretofore unknown herpesvirus GREs shown in Table 1. Preferably, the isolated DNA of the invention shares at least about 60% homology, more preferably, at least about 70%, even more preferably, at least about 80%, yet more preferably, at least about 90%, and even more preferably, greater than 90% homology with any one of the herpesvirus GREs shown in Table 1.

The number of nucleotides positioned between the two hexanucleotides in the isolated DNA of the invention may be from at least about five nucleotides to as many as about twenty nucleotides. Preferably, the number of nucleotides positioned between the two hexanucleotide sequences is from at least about five to about eighteen nucleotides and most preferably, the number of nucleotides positioned between the two hexanucleotide sequences is from at least about six to about eighteen nucleotides.

As used herein, by an isolated herpesvirus GRE is meant a DNA sequence comprising the GRE which is separated from components which naturally accompany it, including the sequences which flank it in a naturally occurring state, e.g., a DNA fragment which has been removed from the sequences which are normally adjacent to the fragment, e.g., the sequences adjacent to the fragment in a genome in which it naturally occurs. The term also applies to a DNA which has been substantially purified from other components which naturally accompany the nucleic acid, e.g., RNA or DNA, protein or lipid which naturally accompany it in the cell.

Further, as used herein, the term homologous refers to the subunit sequence similarity between two polymeric molecules e.g., between two nucleic acid molecules, e.g., between two DNA molecules. When a subunit position in both of the two molecules is occupied by the same monomeric subunit, e.g., if a position in each of two nucleic acid molecules is occupied by adenine, then they are homologous at that position. The homology between two sequences is a direct function of the number of matching or homologous positions, e.g., if half (e.g., 5 positions in a polymer 10 subunits in length) of the positions in two nucleic acid sequences are homologous then the two sequences are 50% homologous; if 70% of the positions, e.g., 7 out of 10, are matched or homologous, the two sequences share 70% homology. By way of example, the nucleic acid sequences GAATTC and GAAGGT share 50% homology.

By substantially homologous, as used herein referring to a nucleic acid sequence, is meant DNA sequence which shares at least 60% homology with another DNA sequence. Preferably, the DNA sequence is 70% homologous, more preferably, it is 80% homologous and most preferably, it is at least 90% homologous with the other DNA sequence.

The isolated GRE of the invention may be obtained either by direct synthesis of the sequence of the GRE, or it may be obtained by first cloning the Group II sequence comprising the GRE in a suitable vector, amplifying the clone and then isolating the sequence of the GRE from the clone. Methods for synthesis of nucleic acids are well known in the art as are methods for cloning of nucleic acids (see for example, Sambrook et al., 1989, Molecular Cloning: A Laboratory Manual, Cold Spring Harbor, N.Y.). To clone the herpesvirus GRE of the invention, a fragment of DNA comprising the desired sequence is inserted into a suitable vector using ordinary molecular biology techniques. Suitable vectors include those designed to yield large quantities of DNA comprising the GRE. Such vectors are available commercially and the techniques involved in cloning of DNA are familiar to any ordinary molecular biologist and are described in Sambrook et al. (1989, Molecular Cloning: A Laboratory Manual, Cold Spring Harbor, N.Y.).

The invention also includes an isolated nucleic acid sequence complementary to a DNA sequence comprising two consensus hexanucleotide glucocorticoid receptor binding sequences having at least six nucleotides positioned therebetween. The isolated nucleic acid sequence of the invention shares preferably about 60% complementarity with, more preferably, at least about 70%, even more preferably, at least about 80%, yet more preferably, at least about 90%, and even more preferably, greater than 90% complementarity with one of either or the two DNA strands of the herpesvirus GREs shown in Table 1. Typically, the isolated nucleic acid is from 18 to 100 contiguous nucleotides in length, more typically the isolated nucleic acid is from 18 to 80 nucleotides in length; however; the isolated nucleic acid may have from about 18 to 70, 18 to 60, 18 to 50, 18 to 40, 18 to 30, 18 to 20 nucleotides in length; or, the isolated nucleic acid may even consist of 18 nucleotides in length or less provided that the isolated nucleic acid disrupts the function of the target GRE. The isolated nucleic acid may be RNA or DNA. Tests for disruption of the function of the GRE are described herein and include, for example, tests for DNA replication, viral transcription, GR binding to GRE sequences, and in vitro and in vivo tests for virus replication and reactivation.

Complementary as used herein refers to the subunit sequence complementarity between two nucleic acids, two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs).

In the context of this invention, the isolated nucleic acid comprises a nucleotide polymer (an oligonucleotide) consisting of naturally occurring bases, sugars and backbone linkages. The nucleotide polymer may also include non-naturally occurring monomers which function similarly to the original nucleotides in their binding characteristics. Modified or substituted nucleotides may be preferable to the naturally occurring nucleotides in that they may exhibit increased stability in the presence of nucleases, enhanced cellular uptake, and/or increased binding affinity for the target nucleic acid and other features which render them potentially more successful as therapeutic agents. Assessment of nuclease resistance enhanced cellular uptake and binding affinity for a target sequence are procedures which are routinely available to the skilled artisan. Increased resistance to nucleotides, enhanced cellular uptake and enhanced binding of the oligonucleotide to the target DNA should serve to enhance inhibition of HSV replication and reactivation of virus from the latent state.

Oligonucleotides which contain at least one phosphorothioate modification are known to confer upon the oligonucleotide enhanced resistance to nucleases. Specific examples of modified oligonucleotides include those which contain phosphorothioate, phosphotriester, methyl phosphonate, short chain alkyl or cycloalkyl intersugar linkages, or short chain heteroatomic or heterocyclic intersugar ("backbone") linkages. In addition, oligonucleotides having morpholino backbone structures (U.S. Pat. No. : 5,034,506) or polyamide backbone structures (Nielsen et al., 1991, Science 254: 1497) may also be used.

The examples of oligonucleotide modifications described herein are not exhaustive and it is understood that the invention includes additional modifications of the oligonucleotides of the invention which modifications serve to enhance the therapeutic properties of the oligonucleotide without appreciable alteration of the basic sequence of the oligonucleotide.

Methods of preparing the oligonucleotides used in accordance with this invention are routine in the art, for example, solid phase synthesis is a well known technique commonly used to synthesize such oligonucleotides. It is also well known to use similar techniques to prepare other oligonucleotides such as phosphorothioate and alkylated derivatives.

The invention further includes antibodies and peptides, independently generated or derived from antibodies, directed against the isolated herpesvirus GRE of the invention which may be useful in inhibition of herpesvirus replication and reactivation and therefore as therapeutic compositions for treatment of herpesvirus infections.

To generate such antibodies, the isolated herpesvirus GRE of the invention is obtained as described herein, and polyclonal antibodies directed against the DNA are generated using standard technology available in the art described for example, in Harlow et al. (1988, In: *Antibodies*, A Laboratory Manual, Cold Spring Harbor, N.Y.). For example, rabbits may be inoculated with the isolated herpesvirus GRE of the invention at a dose of about 50 µg per animal), which GRE is complexed with about 75 µg methylated bovine serum albumin or other suitable protein, and emulsified complete Freund's adjuvant, or other suitable adjuvant, as described by Lafer et al. (1981, Proc. Natl. Acad. Sci. USA 78:3546–3550). Serum from animals so inoculated is obtained at regular intervals, beginning at about 45 days post inoculation, and antibody contained therein is assessed for the ability to bind to the subject GRE using standard procedures (Harlow et al. (1988, In: *Antibodies*, A Laboratory Manual, Cold Spring Harbor, N.Y.). Alternatively, monoclonal antibodies may also be generated to DNA molecules using standard hybridoma technology available in the art (Lafer, 1988, J. Mol. Biol. 203(2):511–516).

Further, if the DNA is obtained in relatively abundant quantities, polyclonal antibodies can be generated following the protocol of Jones et al. (1987, *Cell* 48:79), wherein the DNA is first injected into rabbit lymph nodes followed by subcutaneous booster inoculations at regular intervals. Both preimmune serum and serum obtained after each booster can be assayed for activity against the appropriate DNA using any one of several methods known to those skilled in the art, such as immunoprecipitation, an enzyme-linked immunosorbent assay (ELISA), radioimmunoassay (RIA), or even an Ouchterlony double diffusion assay.

Antibodies directed against the Group II GREs of the invention may also be made by inoculating rabbits as described above, with GRE protein complexes. GRE protein complexes which are formed in infected cells may be different from those formed in uninfected cells. Antibodies which are directed to infected cell GRE complexes may therefore be capable of inhibiting the function of the Group II GRE, while having no effect on a Group I GRE. Thus, administration of an antibody to a animal being immunosuppressed with a glucocorticoid, which antibody is raised against a Group II protein complex, may have the desired effect of inhibiting replication and reactivation of virus in the animal while having no effect on the immunosuppression.

The latter type of antibody is obtained as either a monoclonal or a polyclonal antibody essentially as described above. However, in this case, the material used for inoculation comprises a Group II GRE protein complex. This complex may be obtained in several different ways. For example, the complex may be obtained by mixing in vitro, an infected cell extract with a DNA fragment comprising the GRE, separating the complex so formed in a gel shift assay, excising the complex from the gel and directly inoculating the animal with the complex so excised. Alternatively, plasmid containing the subject GRE is added to cells which are then superinfected with a herpesvirus. The DNA protein complex is extracted from the cells, purified and used to inoculate the animal.

Also encompassed by the invention are compositions comprising small molecules which may be useful in inhibition of herpesvirus replication and reactivation and therefore as therapeutic compositions for treatment of herpesvirus infections. These molecules comprise known or heretofore unknown small molecules, such as analogs of glucocorticoids, for example, dexamethasone analogs, which are capable of effecting immunosuppression in a patient while preventing replication and reactivation of a herpesvirus. Glucocorticoid analogs known to those skilled in the art and heretofore unknown small molecules (derived for example, from proprietary or non-proprietary libraries of molecules) may be first tested in the in vitro assays described herein, such as a DNA replication assay, a transcription assay, or a gel-shift GRE binding assay, for their ability to disrupt herpesvirus GRE function in vitro. Molecules which disrupt GRE function in vitro are predicted to be capable of interfering with GRE function in vivo. Molecules which are predicted to be capable of interfering with GRE function in vivo are tested in the in vivo assays described herein, for example, the in vivo virus replication assay and the in vivo virus reactivation assay. Molecules which interfere with virus replication and/or reactivation in vivo are candidate antiviral compounds which may then be tested in humans.

Thus, the invention should be construed to include compositions comprising small molecules, for example, glucocorticoid analogs, oligonucleotides which are complementary to a Group II GRE and antibodies directed against Group II GREs or Group II GRE protein complexes, each of which is predicted, based on the in vitro and the in vivo assays described herein, or on common knowledge, be capable of preventing replication and reactivation of a herpesvirus in an animal while having either no effect or minimal effect on glucocorticoid function in that animal, in the event that the animal naturally produces such glucocorticoids or is artificially administered such glucocorticoids.

A simple cell culture assay can be used to determine whether the compositions, oligonucleotides and antibodies of the invention are capable of inhibiting replication of a herpesvirus. Alternatively, in vitro assays such as gel-shift assays and DNA replication assays (described herein), affinity chromatography (standard technology in the art) etc., may also be used to examine the effect of the compositions, oligonucleotides and antibodies on virus replication. A composition, an oligonucleotide or an antibody determined to have an effect on virus replication is a candidate antiviral compound potentially capable of inhibiting virus reactivation.

In a cell culture assay, the composition, the oligonucleotide or antibody is added to a culture of cells in a formulation that permits entry of the compound into the cell. Transfection of cells with nucleic acid sequences is common in the art and methods of transfection are described in Sambrook et al. (Molecular Cloning: A Laboratory Manual, Cold Spring Harbor, N.Y.) and in Current Protocols in Molecular Biology (Ausubel et al, 1988, Current Protocols in Molecular Biology. John Wiley and Sons, N.Y.). Similarly, proteins and peptides can be added to cells using the technique of scrape-loading (Fechheimer et al., 1987, Proc. Natl. Acad. Sci. USA 84:8463) or alternatively, certain proteins or peptides can be taken up by cells directly (Frankel et al., 1988, Cell 55:1189; Green et al., 1988, Cell 55:1179; Meek et al., 1990, Nature 343:90). The compositions, the oligonucleotides and antibodies are added to the cells either before or after the cells are infected with the appropriate virus. The effect of the compounds on virus replication may be assessed in a conventional plaque or burst assay, by immunofluorescent techniques, or by assaying for vital DNA replication as described herein. Compounds that inhibit virus replication can then be tested for their ability to inhibit virus replication and pathogenesis, and tested for toxicity in animal models according to standard methods.

To test the effect of the test compounds on virus replication in vivo, mice are inoculated intercranially (i.c.) or intraperitonelly (i.p.) with serial dilutions of virus. The i.c. or i.p. $LD_{50}$ (that amount of virus resulting in 50% survival of animals) is recorded (Melnick et al., 1976, Cancer Research 36: 845–856). Mice are then infected with an appropriate amount of virus to effect efficient virus replication, and either prior to, during, or following infection, a glucocorticoid such as dexamethasone (DEX) in the presence or absence Of the test compound is administered to the mice (Shimeld et al., 1990, J. Gen. Virol. 71:397–404). Control mice are sham-treated with saline. The $LDs_{50}$ is then determined and the effect of the test compound on levels of virus replication is assessed by plaque assay.

To test the effect of the test compound on virus reactivation, using the mouse eye model, mice are infected with virus (Leib et al., 1989, J. Virol. 63:2893–2900) and either prior to, during, or following infection, dexamethasone is added in the presence or absence of the test compound. Virus reactivation is assessed in explanted ganglia as described herein and the effect of the test compound on virus reactivation is assessed as a measure of the number of ganglia producing reactivated virus and the length of time for reactivation of virus from ganglia.

To assess the effect of the test compound on the efficiency of reactivation, the amount of virus used in the test will comprise serial dilutions of that amount of virus determined to cause reactivation from 50% of the explanted ganglia in the assay (Leib et al., 1989, J. Virol. 63:2893–2900). Mice may be administered the test compound at a concentration of 0.1 µg/kg/day to 5 mg/kd/day depending on the type of compound used. Preferably initially, the test compound is administered intraperitoneally although other routes of administration may also be used. The compound is administered to the mouse at one to several days prior to explantation of ganglia. Ganglia are then explanted and are cultured in medium in the presence or absence of the test compound. If the test compound potentiates virus replication and reactivation, the number of ganglia exhibiting reactivation is expected to be greater, and/or the length of time in which ganglia are observed to reactivate is expected to be shorter in treated mice compared with untreated mice. Conversely, if the test compound inhibits reactivation of the virus, the number of ganglia exhibiting reactivation is expected to be smaller, and/or the length of time in which ganglia are observed to reactivate is expected to be longer in treated mice compared with untreated mice.

Further tests may then be conducted to determine whether the compositions and oligonucleotide or antibody of the invention is capable of preventing reactivation of the virus in for example, a mouse, while the mouse is being actively immunosuppressed using a glucocorticoid. In this test, mice are first infected with virus and the immunosuppressive compound is then administered to the mice in combination with the composition or oligonucleotide or antibody of the invention. Control mice include a group of animals which are uninfected and are administered the immunosuppressive compound alone or which are administered the immunosuppressive compound in combination with the composition or oligonucleotide additional of the invention. Additional controls include a group of infected mice which are separately administered the immunosuppressive compound or the composition or oligonucleotide or antibody of the invention. Immunosuppression of the mice is assessed by counting immune cells and testing for a humoral immune response to an unrelated antigen such as bovine serum albumin. Reactivation of virus is assessed using the explanted ganglia mouse eye model described herein. Compounds which prevent reactivation of virus while having no effect on immunosuppression, are candidate antiviral compounds.

Compositions and oligonucleotides and antibodies of the invention that inhibit virus reactivation may be administered to a animal in one of the traditional modes (e.g., orally, parenterally, transdermally or transmucosally, intrathecally), in a sustained release formulation using a biodegradable biocompatible polymer, or by on-site delivery using micelles, gels and liposomes, or rectally (e.g., by suppository or enema). The compounds can be administered to the animal in a dosage of 0.1 µg/kg/day to 5 mg/kd/day, either daily or at intervals sufficient to inhibit virus reactivation and alleviate the symptoms of the disease. Precise formulations and dosages may be determined using standard techniques, by a pharmacologist of ordinary skill in the art.

Antisense oligonucleotides are known to enter cells and to be effective in regulating expression of a target gene against which they are directed. In fact, in at least one instance, administration of an antisense oligonucleotide to a human has resulted in demonstrated efficacy against cytomegalovirus-associated retinitis (Antiviral Agents Bulletin 5: 161–163, 1992; BioWorld Today, December 20, 1993). Thus, antiviral compounds comprising antisense oligonucleotides are considered by those in the art to be both safe and efficacious in humans (Cohen et al., December 1994, Scientific American, pp. 76).

According to the methods described herein, the invention further provides methods of screening candidate antiherpesviral compounds. Such compounds are predicted to interfere with the function of a herpesvirus GRE according to the DNA replication, transcription and DNA binding assays described herein. The compounds are administered to the animal either prior to, during or after infection of the animal with a herpesvirus in the doses and amounts described herein. The level of replication or reactivation of the virus is then measured. A reduced level of replication or reactivation of the virus in the presence of said compound compared with the level of virus replication or reactivation in the absence of the compound is an indication that the compound is an antiherpesviral compound. Compounds mat be screened in such assays for their ability to immunosuppress the animal while preventing replication and reactivation of virus by administering to the animal an immunosuppressive agent in combination with the test compound. Further, compounds may be tested for their ability to ameliorate an established herpesvirus infection by administering the compound to an animal having a latent herpesvirus infection and measuring the level of replication and reactivation of the virus following such administration. In the latter test, compounds are tested in both the presence and in the absence of an immunosuppressive agent in the animal.

EXAMPLES

Cloning of HSV-1 oriL in *E. coli*.

It has heretofore not been possible to clone intact HSV-1 oriL in *E. coli*. Attempts to clone this sequence in E. coli have resulted in a deleted oriL sequence in this bacterium. Weller et al. (1985, Mol. Cell. Biol. 5:930–942) successfully cloned a 2.3 kb fragment containing an intact copy of oriL in a yeast cloning vector. However, propagation in yeast proved to be an impractical source of oriL as the yields were routinely very low. Thus, it has heretofore not been possible to obtain large quantities of oriL for study. The data now described demonstrate successful cloning of intact oriL sequences in an *E. coli* strain, SURE, which contains mutations in a series of genes involved in independent DNA repair pathways shown to be important in the rearrangement and deletion of DNA containing irregular structures such as palindromes. The oriL containing clones propagated in SURE cells contain no deletions as determined by Southern blot hybridization and DNA sequence analysis and are replication-competent in transient DNA replication assays.

Cells and virus used in this Example.

African green monkey kidney cells (Vero) were grown and maintained in Dulbecco's modified Eagle medium (GIBCO Laboratories, Inc., Gaithersburg, Md) (Weller et al., 1983, J. Virol. 45:354–366). The wild-type KOS strain of HSV-1 and the oriL virus, ts+7, derived from KOS were grown and assayed as described (DeLuca, et al., 1985, Mol. Cell. Biol. 5:1997–2008). The isolation of ts+7 is described in Polvino-Bodnar, et al. (1987, J. Virol. 61:3528–3535).

Methods for isolation and characterization of viral DNA.

Viral DNA for use in cloning and Southern blot analysis was isolated essentially as described in Polvino-Bodnar et al. (1987, J. Virol. 61:3528–3535) except that viral DNA was further purified by centrifugation through CsCl at 35,000 rpm for 72 hours at 25° C.

Restriction enzyme fragments of viral DNA were electrophoretically separated on 1.2% agarose gels (or 0.8% agarose gels for transient DNA replication assays), transferred to nitrocellulose and hybridized to $_{32}$P-labeled probes, which probes were generated by nick translation (Sandri-Goldin et al., 1983, Mol. Cell. Biol. 3: 2028–2044).

Cloning of HSV-1 oriL in an undeleted form in bacteria.

The functional characterization of oriL requires the availability of a cloned intact copy of oriL. In the studies described herein, a strain of *E. coli*, designated as SURE, (Promega) was used. This bacterial strain contains a series of mutations which eliminate a number of independent DNA repair pathways, which pathways are directly involved in the rearrangement and deletion of DNA sequences which form irregular structures such as palindromes and which are found in the HSV-1 oriL.

To clone oriL, a 833 bp fragment was generated by PCR which contains the 144 bp oriL palindrome as well as flanking regulatory and downstream noncoding and coding sequences of the two divergently transcribed genes, ICP8 and DNA polymerase (FIG. 1C). Plasmid pOS5-822 containing oriS is described in Wong et al. (1991, J. Virol. 65: 2601–2611). Plasmid pOL-833 was generated as follows: PCR was used to generate the 833 bp fragment containing oriL to which additional sequences were added to the 5'end of each primer to create new restriction sites in order to facilitate cloning. The reaction conditions used were essentially as described by the manufacturers of the GeneAmp PCR Reagent Kit (Perkin Elmer Cetus, Norwalk, Conn.). One nanogram of KOS DNA was used for amplification. The two primers used were:

Primer #1: 5'CGGAATTCCGTGGTTGCCGTCT-TGGGCTTT 3'[SEQ ID NO3].

Primer #2: 5'CCCAAGCTTGGGGCCGCCGACTTTC-CTCCGG 3'[SEQ ID NO3].

Primer #1 contains an EcoRI site whereas primer #2 contains a HindIII site (FIG. 1B). The PCR-generated fragments were digested with EcoRI and HindIII, cloned into pGEM7Z (f+) Promega, Madison, Wis.) and amplified in *E. coli* SURE cells (Stratagene, La Jolla, Calif.). Plasmid amplification in *E. coli* was minimized (12 to 14 h). Amplified plasmids were purified by standard methods, and then further purified by centrifugation twice through CsCl. Plasmid pOL-433 was generated by digesting pOL-833 with XmaI and BamHI, isolating the 433 bp oriL-containing fragment and then ligating this to XmaI and BamHI digested pGEM7Z(f+) (FIG. 1C). The resulting plasmid was propagated and purified as described above. All plasmids were sequenced by the dideoxynucleotide method. The viral DNA insert in pOL-833 contained no detectable deletions upon amplification in SURE cells as determined by polyacrylamide gel and nucleotide sequence analysis.

Figure 2B:
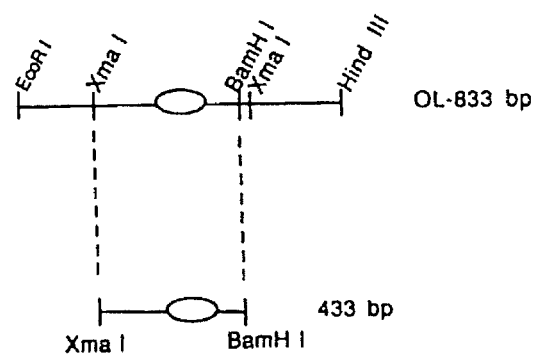

To confirm the absence of deletions in pOL-833 DNA, the viral DNA insert in this plasmid and the corresponding fragments from KOS and ts+7 DNA were digested with XmaI and BamHI and analyzed by Southern blot hybridization (FIG. 2). Mutant ts+7 DNA is wild type at the temperature sensitive locus and contains a 150 bp deletion in oriL (Polvino-Bodnar et al, 1987, J. Virol. 61:3528–3535). Digestion of KOS DNA with XmaI and BamHI yielded a fragment of the expected size (433 bp) (FIG. 2), whereas the 283 bp ts+7 fragment migrated with a greater mobility. The viral DNA fragment derived from pOL-833 migrated with the same mobility as the KOS DNA fragment. Moreover, no evidence of faster migrating (deleted) fragments was observed, even after longer exposure of the blot, suggesting that the oriL containing plasmid had sustained no deletions upon propagation in SURE cells.

DNA Replication assay.

Vero cells ($2 \times 10^6$) were plated in 100-mm dishes and incubated at 37° C. overnight. Four hours prior to transfection, the medium was replaced with fresh medium. Cells were cotransfected with 10 µg of test plasmid and 10 µg of an internal, nonreplicating transfection standard (pUC19) by the calcium phosphate-BES method (Ausubel et al., Supra). Eighteen to 24 hours post-transfection, cells were infected with HSV-1, strain KOS, at a multiplicity of infection (moi) of 10 plaque forming units (PFU)/cell. Except where indicated, cells were harvested and total cellular DNA was isolated 24 hours post-infection (Wong et al., 1991, J. Virol. 65: 2601–2611). DNA (10 µg) was digested with DpnI to restrict unreplicated input DNA and with EcoRI to linearize both test and reference plasmids. The digested DNAs were fractionated on 0.8% agarose gels, transferred to nitrocellulose, and hybridized to $^{32}$P-labeled, nick-translated vector sequence (pUC19). The resulting bands were quantitated using a phosphorimager (Molecular Dynamics, Sunnyvale, Calif.).

In order to detect low levels of viral DNA replication in experiments performed to examine the kinetics of replication, the Lipofectin Reagent (Gibco/BRL, Gaithersburg, Md.) method of transfection was used. For these experiments, Vero cells were seeded as described above. At the time of transfection, plasmid DNA (10 µg) was diluted in 2 ml of serum free Dulbecco's modified Eagle's medium. Lipofectin reagent (final concentration 8 µg/ml) diluted in 2 ml of serum-free medium was mixed with the diluted DNA, and the mixture was held at room temperature for 15 minutes. Monolayers were rinsed once with serum-free medium and the DNA mixture was added dropwise to the cells. The monolayers were incubated at 37° C. for 5 hours, at which time the monolayer was rinsed two times with TBS (137 mM NaCl, 5 mM KCl, 25 mM Tris-HCL [pH 7.4]) and fresh medium containing serum was added to the cells. Eighteen to 24 hours after transfection, the cells were infected with KOS at a moi of 10 PFU/cell and total DNA was harvested at 3, 6, 9, 12, and 24 hours post-infection.

Ten micrograms of DNA was digested with either EcoRI and DpnI or with EcoRI and MboI. EcoRI linearizes the test plasmids. DpnI digests unreplicated methylated DNA, whereas MboI digests only replicated unmethylated DNA. Therefore the newly replicated DNA is cleaved and the level of input DNA can be calculated following digestion with MboI. The DNAs were analyzed by Southern blot hybridization as described above.

Functional analysis of oriL-containing plasmids.

Figure 3A:
FIG. 3 comprising parts (A), (B) and (C) depicts results of experiments analyzing the relative replication efficiencies of oriL-containing plasmids pOL-833 and pOL-433 relative to an oriS-containing plasmid, pOS-822. (A) Southern blot analysis of a DNA replication assay. Vero cells were transfected with DNA comprising an internal standard plasmid, pUC19 (mock), or pUC19 DNA and either pOS-822, pOL-833 or pOL-433 DNAs. Total cellular DNAs were harvested 24 hours after infection with KOS. DNA was digested with EcoRI and DpnI, separated on 0.8% agarose gel and hybridized to a $^{32}$P-labeled pUC19 probe. The bracket denotes the bands of replicated DNA. The lower bands represent DpnI digested input DNA. (B) Comparison of levels of DNA (pUC19) from the experiment described in (A). The experiment performed was the same as described in (A) except that the DNA was digested only with EcoRI in order to linearize the plasma DNA. (C) Relative replication efficiencies of ori-containing plasmids. The replicated DNAs in the Southern blot in (A) were quantitated by phosphorimager scanning and the results are presented as fold-amplification over input DNA.
Figure 3B:
Figure 3C:
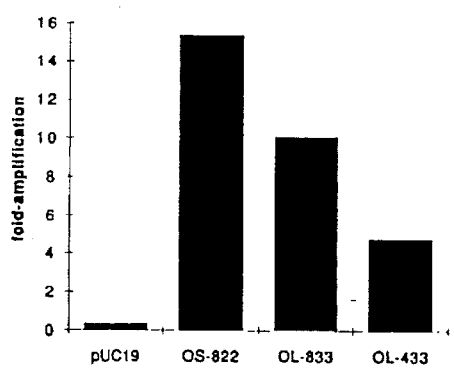

To determine whether the cloned oriL sequences in pOL-833 were functional, transient replication assays were performed (FIG. 3). Veto cells were transfected with either a plasmid containing an 822 bp oriS-containing fragment (Wong et al., 1991, J. Virol. 65:2601–2611) or a plasmid containing the 833 bp oriL containing fragment. In addition, a 433 bp oriL-containing XmaI to BamHI fragment (FIGS. 1C, 2B) cloned into the equivalent site in pGEM7Z(f+), pOL-433, was tested for origin function. A nonreplicating reference plasmid (pUC19) was included to control for transfection efficiency and to serve as an internal standard in the calculation of replication efficiencies (FIG. 3B). The replicated DNAs (bracket, FIG. 3A) were quantitated by phosphorimager scanning, corrected for differences in transfection efficiencies, and the results are presented as fold-amplification over input DNA in the graph shown in FIG. 3C.

As shown in FIG. 3A and 3B, pOS-822, containing 822 bp of oriS sequence, replicated 15-fold more efficiently than the reference plasmid. The replication efficiency determined here is similar to that reported previously for pOS-822 (Wong et al. 1991, J. Virol. 65: 2601–2611) in which it replicated 16- to 22-fold more efficiently than the reference plasmid. In contrast, pOL-833 containing oriL replicated approximately two-thirds as efficiently as the oriS-containing plasmid, but approximately 10-fold more efficiently than the reference plasmid.

Discovery of HSV-1 GREs.

The availability of large quantities of oriL has made possible a study of oriL function in various cell types, some of which resemble those in which the virus replicates during productive infection in vivo and others of which resemble those cells in which the virus remains latent during latent infection in vivo.

PC12 cells are cells cloned from a transplantable rat pheochromocytoma. An important feature of these cells is that after several days exposure to NGF they undergo a dramatic change in phenotype and acquire a number of properties characteristic of sympathetic neurons; they cease to proliferate, grow long neurites, become electrically excitable, and exhibit a number of changes in composition associated with enhanced neuronal differentiation. Thus, PC12 cells resemble cells in which HSV-1 is latent in vivo.

Vero cells are an immortalized line of African Green Monkey kidney cells comprising primate epithelial cells. These cells resemble those cells in which HSV-1 undergoes productive infection in vivo.

Figure 4:
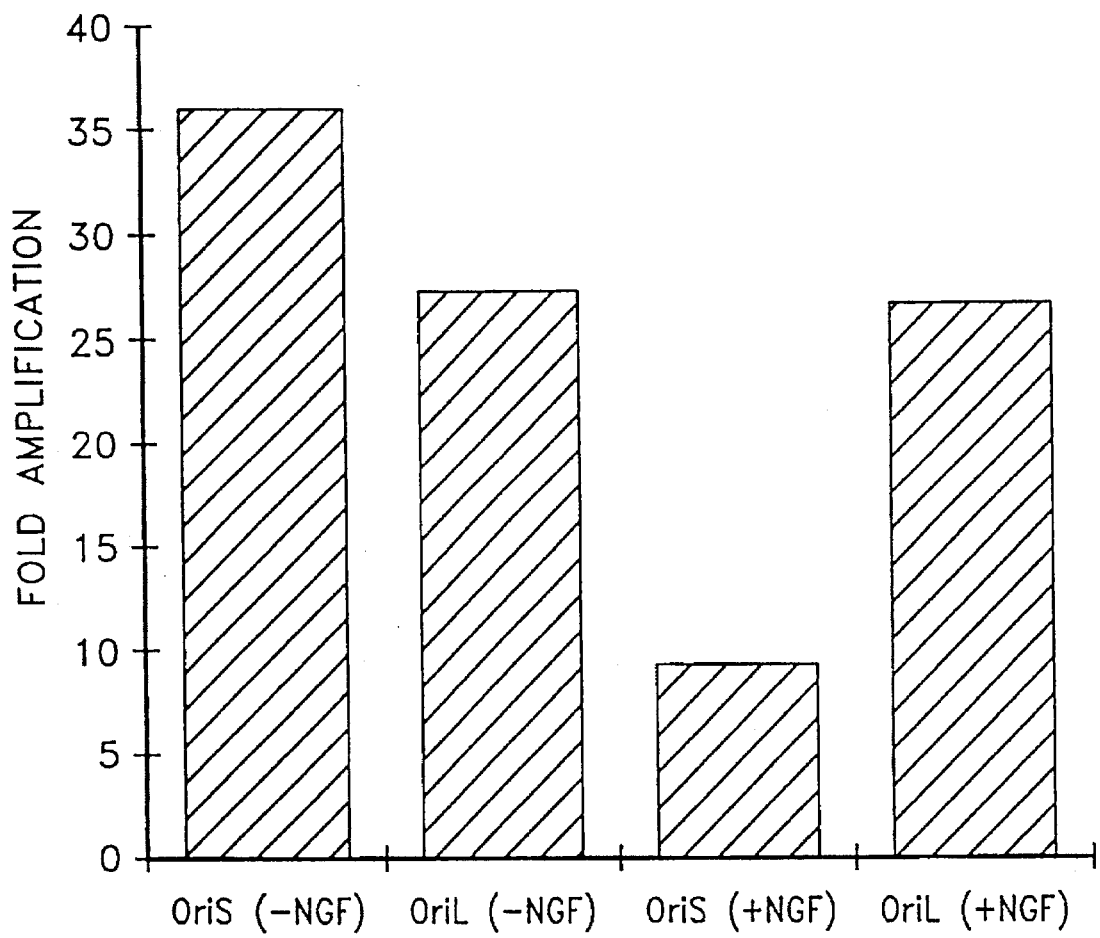
FIG. 4 is a graph depicting the relative replication efficiencies of oriL and oriS-containing plasmids in undifferentiated and in differentiated PC12 cells. The graph summarizes data obtained in transient DNA replication assays using Southern blot analysis. PC12 cells were transfected with 10 µg of either an oriL-containing plasmid (pOL-833) or an oriS-containing plasmid (pOS-822) using Lipofectin. Five hours post-transfection, cells were rinsed and fresh media was added which either contained or did not contain nerve growth factor (NGF) (100 ng/ml) as indicated. Six days after the addition of NGF, cells were infected with KOS (multiplicity of infection (moi) of 10) in the appropriate media (i.e., with or without NGF) and total cellular DNA was harvested at 24 hours post-infection and processed for a DNA replication assay as described herein. Ten micrograms of DNA were digested with either EcoRI and DpnI to quantitate replicated DNAs or with EcoRI and MboI to quantitate input DNAs. The digested DNAs were analyzed by Southern blot hybridization using a $^{32}$P-labelled pUC19 probe. The replicated input DNAs were quantitated by phosphorimager scanning analysis and the results are presented as fold amplification over input DNA.

The replication efficiency of oriS and oriL was compared in undifferentiated PC12 cells and in Vero cells using a transient replication system. The results obtained in either cell type were similar in that, oriS replicated slightly more efficiently than oriL (FIG. 4). However, when replication was examined in PC12 cells treated with NGF, oriL replicated to approximately the same levels as had been observed in undifferentiated cells (FIG. 4; Table 2, which represents the average of four experiments). In contrast to these results, the level of replication of oriS was reduced approximately 5-fold in NGF-treated cells (FIG. 1; Table 2, which represents the average of five experiments).

TABLE 2

Fold-Difference in the Replication Efficiency of OriS and OriL-Containing Plasmids in Differentiated Compared with Undifferentiated PC12 Cells.

|  | oriS | oriL |
| --- | --- | --- |
| Exp. #1 | ↓ 7.6 X[a] | ↓ 1.7 X |
| Exp. #2 | ↓ 3.8 X | No change |
| Exp. #3 | ↓ 5.5 X | No change |
| Exp. #4 | ↓ 2.0 X | ↓ 1.3 X |
| Exp. #5 | ↓ 4.2 X | — |
| Avg. | ↓ 4.6 X | ↓ 1.2 X |

[a]The results of five separate experiments performed as described in the legend to FIG. 4. The replicated and input DNAs were quantitated by phosphorimager scanning analysis and the results are presented as fold-difference in replication in differentiated cells compared to undifferentiated cells. Avg. is the average change for the five experiments.

To establish a molecular basis for the difference in replication levels between oriL and oriS, a computer search of the nucleotide sequence of oriL and associated flanking sequences was conducted. The search was formulated to discover whether binding sites for transcription factors, other than those already discovered, are contained within the oriL sequence. The search was conducted using a relational database of transcription factors according to that described by Ghosh (1990. NAR 18:1749–1756).

Figure 5:
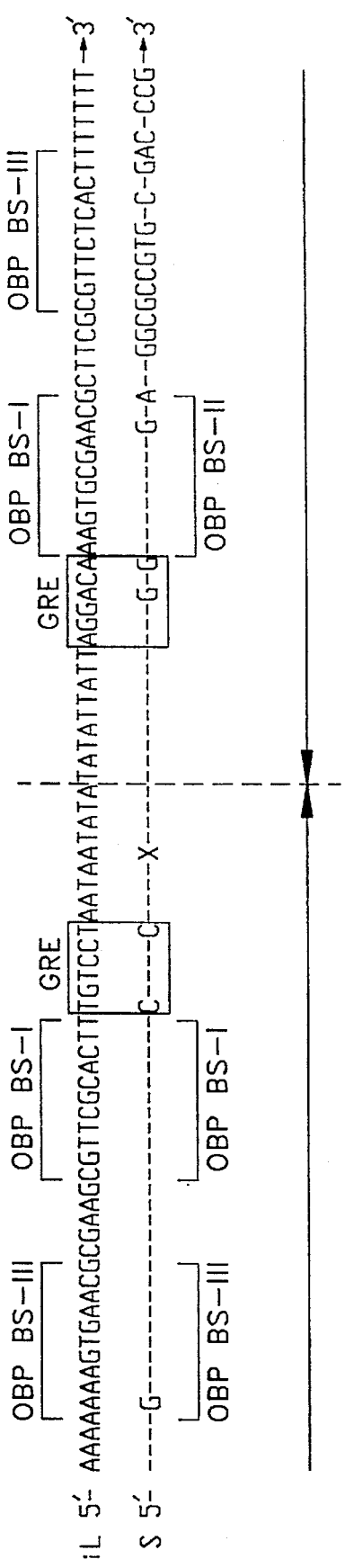
FIG. 5 is a diagram of the sequences of the oriL [SEQ ID NO:3] and oriS [SEQ ID NO:5] palindromic regions in HSV-1 DNA. The location hexanucleotides present in the oriL GRE is shown (indicated by boxes) as are the locations of the binding sites of the origin binding proteins (OBP BS-I, OBP BS-II and OBP BS-III. The vertical dashed line represents the center of dyad symmetry of the palindromes. Dashed lines in the oriS sequence represent nucleotides which are identical in oriL and oriS.
Figure 7A:
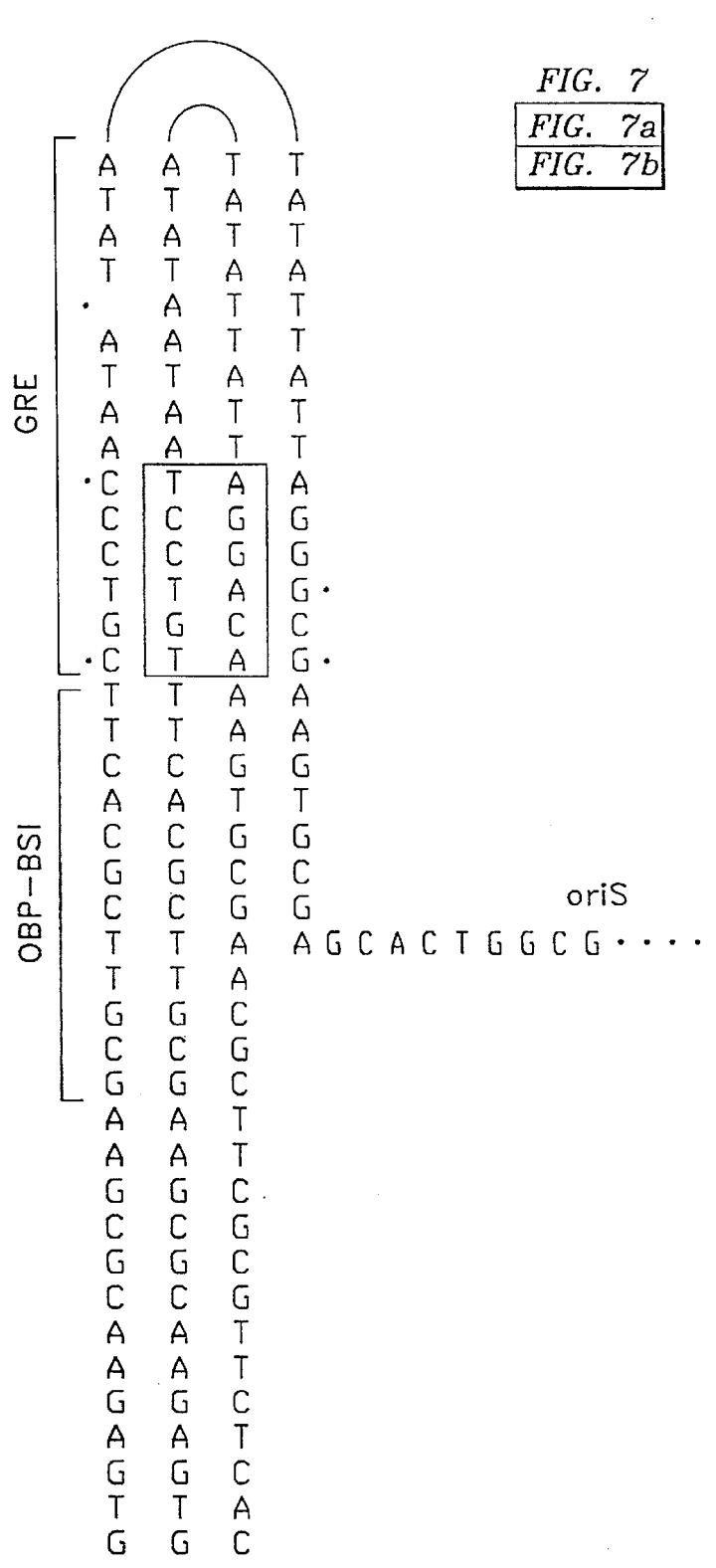

A GRE was discovered to be positioned within the palindrome of oriL immediately adjacent to the origin binding protein (OBP) site I (FIG. 5). The known consensus GRE is a 15 bp perfect palindromic sequence comprising two hexanucleotides separated by three nucleotides (FIG. 6). However, the GRE found in oriL is unique in that the two consensus hexanucleotides are reversed with respect to those in the consensus sequence, i.e., the TGTT/CCT hexanucleotide is located 5' to the AGA/GACA hexanucleotide in oriL, whereas in the consensus sequence, the AGA/GACA hexanucleotide is located 5' to the TGTT/CCT hexanucleotide (FIG. 6). Further, the spacing between the two hexanucleotides of each of these GREs also differs in that in oriL, eighteen nucleotides separates both hexanucleotides, whereas in the consensus sequence, only three nucleotides separate each hexanucleotide. In oriL, these eighteen nucleotides consist of contiguous AT nucleotides which are palindromic (FIG. 6 and 7).

Purified glucocorticoid receptor protein (GR) binds as a dimer to the consensus GRE (Hard, et al, 1990, Biochemistry 29:5358–5364; Hollenberg et al., 1985, Nature 318:635–641). Initial binding to the 3' hexanucleotide (TGTTCT) portion of the GRE is followed by cooperative binding of a second GR molecule to the 5' (GGTACA portion of the GRE (Tsai et al, 1988, Cell 55:361–369).

To determine whether the GRE located in HSV-1 oriL plays a role in DNA replication of the virus, PC12 cells were transfected with plasmids containing either oriL or oriS sequences in the presence or absence of dexamethasone and NGF. Dexamethasone is known to activate GR. Formation of glucocorticoid/receptor complex in the cytoplasm is followed by translocation of this complexes to the nucleus. Dexamethasone/receptor complexes within the nucleus bind to a GRE and activate transcription of cellular genes. An increase in the level of replication of the oriL-containing plasmid was observed in PC12 cells treated with dexamethasone compared with cells which were not so treated. This increase was approximately 1.6-fold higher in dexamethasone-treated undifferentiated cells (average of three experiments) and approximately 5.0-fold higher in dexamethasone-treated differentiated PC12 cells (average of four experiments) compared with untreated cells (Table 2). Replication of the oriS-containing plasmid was reduced approximately 2.0-fold in undifferentiated or 4.1-fold in differentiated PC12 cells (average of three or four experiments; Table 3) in the presence of dexamethasone compared to replication in the absence of dexamethasone.

TABLE 3

Fold-Difference in the Replication Efficiency of OriS and OriL-Containing Plasmids in Differentiated compared with Undifferentiated PC12 cells in the Presence compared with the Absence of Dexamethasone.

|  | oriS | oriL |
| --- | --- | --- |
| Undifferentiated | | |
| Exp. #1 | ↓ 2.1 X* | ↓ 1.7 X |
| Exp. #2 | ↓ 1.06 X | ↑ 1.5 X |
| Exp. #3 | ↓ 2.8 X | ↑ 1.5 X |
| Exp. #4 | ↓ 2.0 X | ND |
| avg. | ↓ 2.1 X | ↑ 1.6 X |
| Differentiated | | |
| Exp. #1 (+ NGF) | ↓ 5.7 X | ↓ 2.6 X |
| Exp. #2 (+ NGF) | ↓ 2.6 X | ↑ 4.4 X |
| Exp. #3 (+ NGF) | ↓ 3.9 X | ↑ 4.3 X |
| Exp. #4 (+ NGF) | ND | ↑ 8.9 X |
| Avg. | ↓ 4.1 X | ↑ 5.0 X |

*PC12 cells were transfected with 10 µg of either an oriS- or an oriL-containing plasmid as described in the legend to FIG. 4. Five hours post-transfection, the cells were washed and media containing NGF (100 ng/ml) was added to one set of transfected PC12 cells. At six days after transfection, both the undifferentiated (-NGF) and the differentiated (+NGF) cells were infected with KOS (MOI of 10) either in the presence or absence of dexamethasone (0.5 µM). At twenty-four hours post-infection the cells were harvested and DNA isolated and assayed as described in the legend to FIG. 4. The results are presented as fold-difference in replication in undifferentiated (top) or differentiated (bottom) PC12 cells in the presence of dexamethasone compared to the absence of dexamethasone. Avg. is the average of the separate experiments for undifferentiated or differentiated PC12 cells transfected with either oriS or oriL.

To assess the effect of cell type on dexamethasone-enchanced oriL replication and on dexamethasone-repressed oriS replication, the experiment was repeated in Vero cells (Table 4). In Vero cells, a minimal effect of dexamethasone on oriL or oriS replication was observed compared with PC12 cells. For example, replication of oriL was slightly increased (1.8-fold, average of three experiments) in the presence of dexamethasone compared to replication in its absence; and, replication of oriS was decreased 1.6-fold (average of three experiments) in the presence of dexamethasone compared to replication in the absence of this compound.

TABLE 4

Fold-Difference in the Replication Efficiency of OriS and OriL-Containing Plasmids in Vero cells in the Presence compared with the Absence of Dexamethasone.

|  | oriS | oriL |
| --- | --- | --- |
| Exp. #1 | ↓ 2.3 X* | ↑ 2.3 X |
| Exp. #2 | ↓ 1.3 X | ↑ 2.1 X |
| Exp. #3 | ↓ 1.1 X | ↑ 1.1 X |
| Avg. | ↓ 1.6 X | ↑ 1.8 X |

*Vero cells were transfected with 10 µg of either an oriS-containing plasmid (pOS-822) or an oriL-containing plasmid (poL-833). Eighteen to 24 h post-transfection one set of transfected cells was infected with KOS in the presence of dexamethasone while the other set was infected in the absence of dexamethasone (0.5 µM). Cells were harvested and total cellular DNA was isolated at 24 h post-infection. The DNA was analyzed as described in the legend to FIG. 4. The replicated and input DNAs were quantitated by phosphorimager scanning analysis and the results of three separate experiments are presented as the fold-difference in replication in the presence of dexamethasone compared to the absence of dexamethasone. Avg. is the average change for the three experiments.

Binding of Glucocorticoid Receptor to OriL.

Enhancement of replication of oriL is a direct result of the effect of dexamethasone on GR in that the C-terminal DNA binding domain of GR (Alroy et al., 1992, Nucl. Acids Res. 20:1045–1052) binds to an oriL containing oligonucleotide of 57 nucleotide in length comprising both hexanucleotides separated by the eighteen nucleotide spacer sequence. To establish this, a DNA mobility shift assay was performed FIG. 8; lanes 5–8). To assess binding of GR to oriL GRE and oriL GRE sequences, oligonucleotide probes were synthesized which encompass the oriL GRE, and oriL GRE sequences.

To perform the gel shift assay, increasing concentrations (0–25 ng) of protein was incubated at 25° C. for 30 min with $9 \times 10^4$ cpm of probe (1 ng). Protein-DNA complexes were separated from free probe by electrophoresis at 4° C. in 6% polyacrylamide gels (37.5:1 acrylamide/bisacrylamide) prepared and run in 0.5×TBE (Tris-Borate-EDTA) buffer.

Figure 8:
FIG. 8, comprising parts (A) and (B), depicts binding of glucocorticoid receptor (GR) protein to HSV-1 oriL. (B) Radiolabelled wild type oriL GRE-containing DNA (L) (lanes 5–8) or mutant GRE containing DNA (L/S) (lanes 1–4) were incubated in the presence of increasing concentrations of purified C-terminal glucocorticoid receptor (GR) for 30 minutes at 25° C. Protein-DNA complexes were allowed to form and the resulting complexes were separated on a 6% polyacrylamide gel. The specificity of the complexes formed was confirmed by incubating radiolabelled wild type oriL-containing GRE (lanes 12–14) or mutant GRE (lanes 9–11) DNAs with increasing concentrations of a mutant GR (ER). At the top of the figure, the nucleotide sequence of the probes [SEQ ID NO:10 and 11] used in the gel shift analysis are shown (A). The boxes indicate the two hexanucleotides of the GRE. The dots indicate nucleotides which are changed in the mutant GRE probe (L/S GRE). The dashed lines represent nucleotides which are the same in each oligonucleotide probe.

When the oriL $^-$ probe (L/S GRE; FIG. 8) was assessed for binding to purified GR in a mobility shift assay, no complex was formed even at the highest concentration of GR used (FIG. 8A; lanes 1–4). To further examine the specificity of complex formation, a C-terminal GR mutant peptide was used in the assay. This peptide contains three amino acids which are changed such that the mutant GR now resembles an estrogen receptor (ER) protein rather than a GR (Alroy et al., 1992, Nucleic Acids Research 20:1045–1052).

Both wild type and mutant oriL sequences (L and L/S, respectively) were tested for their ability to bind ER in a gel shift assay (FIG. 8; lanes 9–14). No significant amount of complex formation was observed with either probe.

The effect of Dexamethasone on ICP6 GRE.

Figure 9:
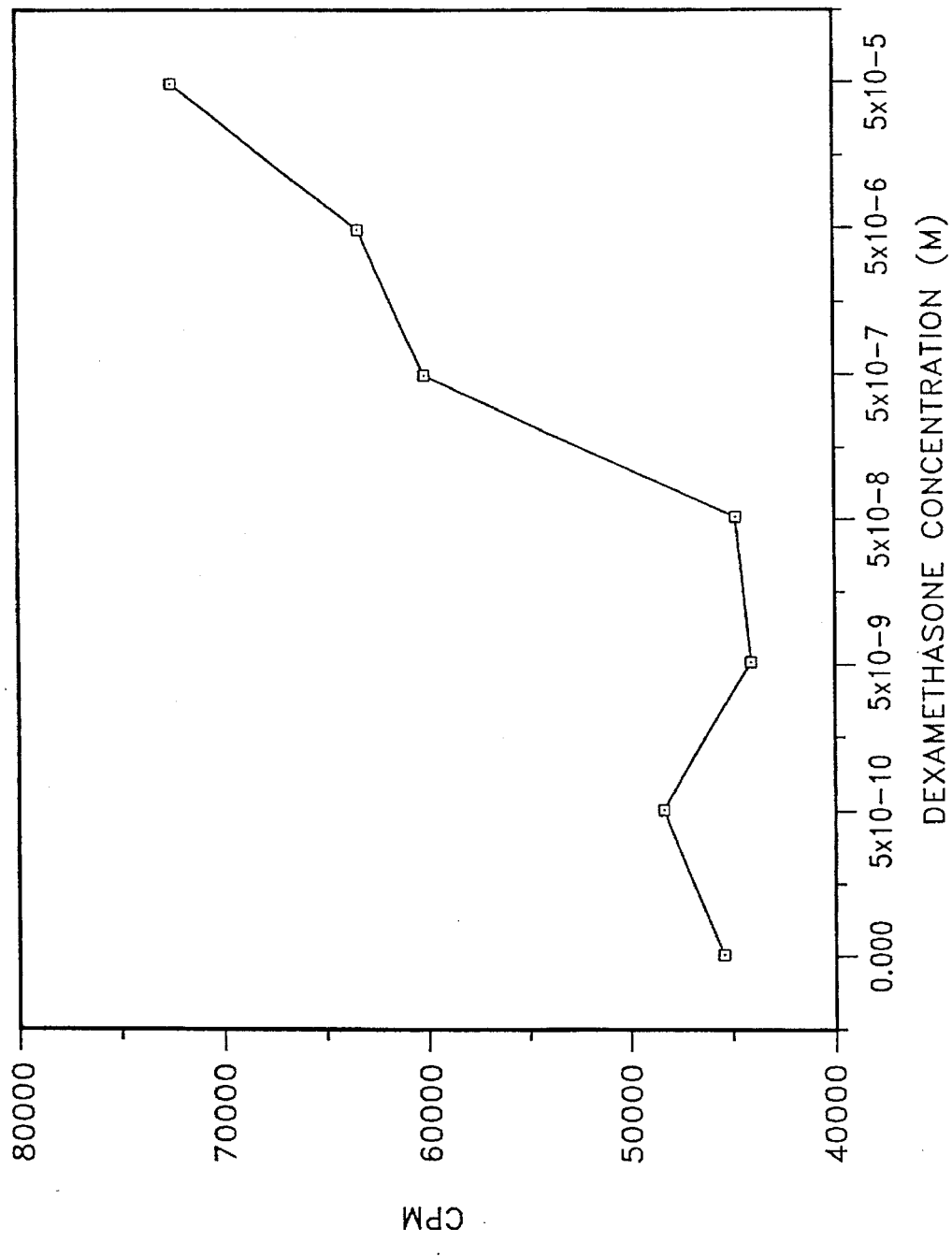
FIG. 9 is a graph depicting the effect of dexamethasone on ICP6 promoter activity. Vero cells (6×10$^5$) were transfected with 10 µg of the plasmid, ICP6CAT, using Lipofectin Reagent. Twenty four hours post-transfection, dexamethasone was added at the indicated concentrations. Eighteen to twenty fours after the addition of dexamethasone, the cells were harvested and the level of expression of chloramphenicol acetyl transferass (CAT) was assessed. The results represent the mean of four separate experiments.

To test the effect of dexamethasone on the GRE located within the ICP6 promoter, a plasmid comprising the ICP6 promoter sequences was fused to the CAT gene. Cells were transfected with this plasmid, dexamethasone was added and the level of expression of CAT was measured. The results, which are presented in FIG. 9, clearly establish that the ICP6 promoter-containing GRE is responsive to dexamethasone.

It is thus apparent from the data presented herein, that the Group II GREs of the invention are responsive to the presence of a glucocorticoid. It is further apparent that the nature of the hexanucleotide intervening sequence, that designated as (N), need not necessarily be palindromic since both the oriL GRE sequence (which is palindromic) and the ICP6 GRE sequence (which is not palindromic) are responsive to glucocorticoid stimulation.

Generation of viral mutants containing a mutated oriL GRE.

To confirm a role for the HSV-1 GRE in the viral life cycle, herpesvirus mutants having a mutation in one or both of the HSV-1 GRE sequences may be generated. The following protocol useful for generation of HSV-1 mutants may be generally adapted to other herpesviruses by those skilled in the art of making viral mutants.

Given that oriL lies within the promoter regulatory elements of the ICP8 gene, to generate herpesvirus mutants containing a defective GRE, marker rescue of a temperature sensitive mutation in the ICP8 viral mutant, tsA24, may be utilized. Cells are cotransfected with tsA24 viral DNA and a plasmid containing a wild type ICP8 gene oriL sequences containing the following mutations in the oriL GRE:

OriL: TGTCCT (N)$_{18}$ AGGACA[SEQ ID NO:2]

OriL GRE$^{-}$ GGTCCC (N)$_{18}$ GGGACG[SEQ ID NO:88].

As viral DNA replicates, mutations in the GRE sequences are recombined into the viral genome by a process known as homologous recombination. During this process, the mutation in the ICP8 gene is also rescued thus providing a means for initial screening of progeny virus in that only the rescued virus will now grow at the nonpermissive temperature of 39.4° C. Since the oriL sequences lie within the ICP8 promoter region, if the ICP8 gene is rescued, then the oriL sequences containing the GRE will also be recombined into the progeny viral genome. Therefore, the only virus growing at 39.4° C. will contain the mutated GRE sequences. Progeny virus should therefore contain a wild type ICP8 gene in addition to a mutated GRE in oriL. Progeny virus are then screened by Southern blot hybridization for the presence of these features taking advantage of the newly created restriction enzyme site (BsmFI) in the mutated oriL GRE which is formed by the aforementioned nucleotide changes. Recombination of mutant DNAs into herpesvirus genomes is well within the skill of the artisan and is described for example, in Polvino-Bodnar, et al. (1987, J. Virol. 61:3528–3535).

To generate viral mutants containing mutations in the HSV-1 ICP6 GRE, a similar approach may be used. Briefly, viral mutants in this region of the genome may be generated through marker rescue of a temperature sensitive mutation in the adjacent (UL38) capsid protein gene, i.e., that encoding the protein VP19C (Pertuiset et al., 1989, J. Virol. 63:2169–2179; Rixon et al., 1990, J. Gen. Virol. 71:1211–1214; Yei et al., 1990, J. Virol. 64:1124–1134). In this case, cells are cotransfected with viral DNA obtained from a ts mutant in UL38 A44ts2, a plasmid containing a wild type UL38 gene and a fragment comprising the adjacent ICP6 GRE sequences which have been mutated as described above for oriL. During the process of homologous recombination, the temperature sensitive mutation in the UL38 gene is rescued, and the mutated ICP6 sequences are recombined into the viral genome. Progeny virus are initially screened for a wild type phenotype (as compared with the ts mutant phenotype), and the presence of the desired ICP mutation is confirmed by Southern blot hybridization analysis.

Viral mutants so obtained may be unable to replicate and reactivate and thus, may be useful for studies on Group II GREs. These viruses, since they are likely to be unable to replicate or reactivate, are also useful as vaccine candidates, i.e., as baseline vital vectors for insertion of additional mutations into the viral genome, which mutations may further render the virus both replication and reactivation deficient.

Assessment of HSV-1 oriL GRE Function.

Assays to ascertain the role of HSV-1 GREs during vital infection in vivo.

A. Response of vital mutants to dexamethasone during acute infection. In the first assay, groups of ten seven week old CD-1 mice are anaesthetized and inoculated intercranially (i.c.) with serial 10-fold dilutions of either wild type HSV-1 (strain KOS), or mutant viruses which lack a functional GRE in oriL (mutant A), in the ICP6 promoter (mutant B), or in both oriL and the ICP6 promoter (mutant C). The i.c. $LD_{50}$ (that amount of virus resulting in 50% survival of animals) is recorded (Melnick et al., 1976, Cancer Research 36: 845–856). The experiment may then be repeated using additional dilutions of virus and additional groups of mice in order to obtain a more precise measurement of the i.c. $LD_{50}$.

To test the effects of the GRE mutations on virus replication in response to glucocorticoid treatment, mice are infected with wild type and mutant viruses and either prior to, during, or following infection, a glucocorticoid such as dexamethasone (DEX) is administered intraperitoneally to the mice at a concentration of about 0.2 mg per mouse (Shimeld et al., 1990, J. Gen. Virol. 71:397–404). Control mice are sham-treated with saline. The $LD_{50}$ is then determined and levels of virus replication are assessed by plaque assay.

B. Response of vital mutants to dexamethasone during latent infection. Using the mouse eye model, mice are infected with mutant or wild type virus as described (Leib et al., 1989, J. Virol. 63:2893–2900). Either prior to, during, or following infection, dexamethasone is added as described herein. Virus reactivation is assessed in explanted ganglia further as described herein and the effect of viral mutations on glucocorticoid-induced replication and reactivation is assessed as a measure of the number of ganglia producing reactivated virus and the length of time for reactivation of virus from ganglia.

Additional Glucocorticoid Compounds and Combination Therapies.

In addition to dexamethasone, several glucocorticoid analogs are currently in broad clinical use as immunosuppressive agents, including cortisol, prednisone, methylprednisolone, fludrocortisone and triamcinolone. These compounds may also be tested according to the methods of the invention for their ability to affect replication and reactivation of a herpesvirus using the procedures known in the art and described herein. The results of such tests are useful in that they are predictive of whether a given immunosuppressive agent useful for immunosuppression of a patient may also cause replication and reactivation of a latent herpesvirus infection. If such an agent is predicted to induce reactivation of virus, as is the case for dexamethasone, then combination therapies may be employed which facilitate immunosuppression of the patient while inhibiting replication and reactivation of virus. Such combination therapies include administration of the immunosuppressive agent in combination with either an isolated nucleic acid complementary to the herpesvirus GRE or an antibody directed against the herpesvirus GRE, or both. Additionally, other existing antiviral compounds may be administered to the patient which are known to diminish or ablate virus replication in a patient. In these tests, RU 486, a drug with known (partial) antiglucocorticoid activity may be included as a negative control.

As a first test to determine the effect of a compound on a herpesvirus GRE, for example, the HSV-1 oriL GRE, PC12 cells are transfected with a plasmid comprising wild-type HSV-1 oriL as described herein. A mutant oriL-containing plasmid may be used as a negative control. Eighteen hours post-transfection, cells are infected with HSV-1 strain KOS at a multiplicity of infection of 10 PFU/cell. At the time of infection, the glucocorticoid to be tested is added to one half of the series of transfected cells at a concentration approximately equivalent to 0.5 μM of dexamethasone and the cells are harvested at eighteen to twenty four hours post-infection. Total DNA is isolated from the cells and plasmid amplification is assessed as described herein.

Alternatively, or in addition, the GRE present in the HSV-1 ICP6 gene is used in the assay. In this instance, a transient transfection assay is performed using a plasmid comprising an intact ICP6 promoter. A plasmid comprising an ICP6 promoter which contains a defective ICP6 GRE, or a plasmid in which the ICP6 GRE is absent is used as a negative control. The promoters are fused to the CAT gene coding sequences and a standard transient expression (CAT) transfection assay is performed in the presence and absence of the test glucocorticoid. Following transfection and superinfection with virus as described above, the level of expression of CAT is assessed. The effect of the glucorticoid compound on promoter strength is assessed as a measure of the level of expression of CAT.

A test compound may next be assessed for its ability to induce GR capable of binding to the GRE in question using the gel shift assay as described herein. Compounds which induce GR such that it binds to a herpesvirus GRE may then be assessed for their effect on virus replication and reactivation in vivo in the replication and reactivation assays described herein. In one type of assay, mice are infected in the eye with HSV-1. Approximately thirty days post-infection, ganglia are explanted from the mice and are cocultivated with permissive Vero cells in the presence or absence of the test compound. The effect of the compound on virus reactivation is assessed as a measure of the number of ganglia from which virus reactivates and the length of time taken for reactivation in the presence of the test compound compared with its absence.

In yet another in vivo assay, mice infected with virus may be administered the test compound, or a placebo control. Ganglia are explanted from the mice and the effect of the compound on virus replication and reactivation is assessed as described herein.

The Group II GREs of the invention and compositions and methods designed to disrupt their function should not be construed as being useful solely during immunosuppression of a host organism. Glucocorticoids are naturally produced in animals in response to a variety of situations including situations involving stress (Davies et al., 1973, Infect. Immun. 8:510–518). It is well known that herpesviruses replicate and reactivate more frequently in individuals undergoing stress than in individuals who are not stressed. Thus, there is also a need for the compositions and methods of the invention in situations where naturally produced glucocorticoids are likely to induce virus replication and reactivation. Such situations include, but are not limited to, those which are known to induce herpesvirus reactivation, for example, stress, menstruation and presence of U.V. light. The compositions of the invention might therefore be equally useful when administered to a patient as a topical or oral formulation for treatment of oral or genital herpesvirus infections.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An herpesvirus glucocorticoid response element having the sequence 5'-TGTCCT $(N)_x$ AGGACA -3', wherein x is five to twenty nucleotides [SEQ ID NO:48.

2. The herpesvirus glucocorticoid response element having the sequence 5'-AGGACA $(N)_x$ TGTCCT -3', wherein x is five to twenty nucleotides [SEQ ID NO:66.

3. The herpesvirus glucocorticoid response element of claim 1 or 2 being from a herpesvirus selected from the group consisting of herpes simplex virus type 1, herpes simplex virus type 2, human cytomegalovirus, human herpesvirus type 6, bovine herpesvirus, herpes virus samairi, murine cytomegalovirus and Ictalurid herpesvirus.

4. The herpesvirus glucocorticoid response element of claim 3, wherein said herpesvirus is selected from the group consisting of herpes simplex virus type 1, herpes simplex virus type 2, human cytomegalovirus and human herpesvirus 6.

5. The herpesvirus glucocorticiod response element of claim 4, wherein said herpesvirus is herpes simplex virus type 1.

6. The herpesvirus glucocorticoid response element of claim 5, wherein said glucocorticoid response element is herpes simplex virus type 1 oriL glucocorticoid response element.

7. The herpesvirus glucocorticoid response element of claim 6, wherein said glucocorticoid response element is herpes simplex virus type 1 ICP6 glucocorticoid response element.

8. The herpesvirus glucocorticoid response element of claim 6, said glucocorticoid response element having the sequence 5'-TGTCCT $(N)_{18}$ AGGACA -3' [SEQ ID NO:2].

9. The herpesvirus glucocorticoid response element of claim 7, said glucocorticoid response element having the sequence 5'-AGGACA $(N)_6$ TGTCCT -3' [SEQ ID NO:3].

10. The herpesvirus glucocorticoid response element of claim 1 or 2, wherein x is six to eighteen nucleotides.

11. An isolated nucleic acid sequence of 18 to 100 nucleotides complementary to a DNA sequence comprising a herpesvirus glucocorticoid response element, said herpesvirus glucocorticoid response element comprising two consensus hexanucleotide glucocorticoid receptor binding sequences having at least five nucleotides positioned therebetween, wherein said hexanucleotide sequence comprises the sequences 5'-TGTCCT-3' and 5'-AGGACA3'.

12. The isolated nucleic acid of claim 11, wherein said herpesvirus glucocorticoid response element is from a herpesvirus selected from the group consisting of herpes simplex virus type 1, herpes simplex virus type 2, human cytomegalovirus, human herpesvirus type 6, bovine herpesvirus, herpes virus samairi, murine cytomegalovirus and Ictalurid herpesvirus.

13. The isolated nucleic acid of claim 12 wherein said herpesvirus is selected from the group consisting of herpes simplex virus type 1, herpes simplex virus type 2, human cytomegalovirus and human herpesvirus type 6.

14. The isolated nucleic acid of claim 13, wherein said herpesvirus is herpes simplex virus type 1.

15. The isolated nucleic acid of claim 14, wherein said glucocorticoid response element is herpes simplex virus type 1 oriL glucocorticoid response element.

16. The isolated nucleic acid of claim 14, wherein said glucocorticoid response element is herpes simplex virus type 1 ICP6 glucocorticoid response element.

17. The isolated nucleic acid of claim 15, said glucocorticoid response element having the sequence 5'-TGTCCT $(N)_{18}$ AGGACA -3' [SEQ ID NO:2].

18. The isolated nucleic acid of claim 16, said glucocorticoid response element having the sequence 5'-AGGACA $(N)_6$ TGTCCT -3' [SEQ ID NO:3].

19. A herpesvirus glucocorticoid response element having the sequence 5' TGTCCT $(N)_{18}$ AGGACA -3' [SEQ ID NO:2].

20. A herpesvirus glucocorticoid response element having the sequence 5'-AGGACA $(N)_6$ TGTCCT -3' [SEQ ID NO:3].

* * * * *